(12) United States Patent
Maccecchini

(10) Patent No.: US 11,382,893 B2
(45) Date of Patent: Jul. 12, 2022

(54) (3AR)-1,3A,8-TRIMETHYL-1,2,3,3A,8,8A-HEXAHYDROPYRROLO[2,3-B]INDOL-5-YL PHENYLCARBAMATE AND METHODS OF TREATING OR PREVENTING NEURODEGENERATION

(71) Applicant: ANNOVIS BIO, INC., Berwyn, PA (US)

(72) Inventor: Maria Maccecchini, West Chester, PA (US)

(73) Assignee: ANNOVIS BIO, INC., Berwyn, PA (US)

( * ) Notice: Subject to any disclaimer, the term of this patent is extended or adjusted under 35 U.S.C. 154(b) by 0 days.

(21) Appl. No.: 16/994,924

(22) Filed: Aug. 17, 2020

(65) Prior Publication Data

US 2020/0375948 A1 Dec. 3, 2020

Related U.S. Application Data

(63) Continuation of application No. 16/504,813, filed on Jul. 8, 2019, now Pat. No. 11,096,926, which is a continuation of application No. 15/450,937, filed on Mar. 6, 2017, now Pat. No. 10,383,851, which is a continuation of application No. 13/041,211, filed on Mar. 4, 2011, now abandoned.

(51) Int. Cl.
| | | |
|---|---|---|
| *A61K 31/407* | (2006.01) | |
| *A61P 25/28* | (2006.01) | |
| *A61K 9/00* | (2006.01) | |
| *A61K 9/20* | (2006.01) | |
| *A61K 9/28* | (2006.01) | |
| *A61K 9/48* | (2006.01) | |

(52) U.S. Cl.
CPC .......... *A61K 31/407* (2013.01); *A61K 9/0053* (2013.01); *A61K 9/20* (2013.01); *A61K 9/2886* (2013.01); *A61K 9/48* (2013.01); *A61K 9/4825* (2013.01); *A61P 25/28* (2018.01)

(58) Field of Classification Search
CPC ...... A61K 31/407; A61K 9/0053; A61K 9/20; A61K 9/2886; A61K 9/48; A61K 9/4825; A61P 25/28
See application file for complete search history.

(56) References Cited

U.S. PATENT DOCUMENTS

| | | | |
|---|---|---|---|
| 5,171,750 A | 12/1992 | Brossi et al. | |
| 5,409,948 A * | 4/1995 | Greig | A61K 31/40 514/411 |
| 6,410,747 B1 | 6/2002 | Greig et al. | |
| 6,495,700 B1 | 12/2002 | Bruening et al. | |
| 6,683,105 B2 | 1/2004 | Greig et al. | |
| 7,153,882 B2 | 12/2006 | Grieg et al. | |
| 7,625,942 B2 | 12/2009 | Bruinsma et al. | |
| 7,786,162 B2 | 8/2010 | Grieg et al. | |
| 7,994,210 B2 | 8/2011 | Bruinsma et al. | |
| 8,258,172 B2 | 9/2012 | Greig et al. | |
| 8,691,864 B2 | 4/2014 | Greig et al. | |
| 2002/0094999 A1 | 7/2002 | Grieg et al. | |
| 2004/0024043 A1 * | 2/2004 | Greig | A61P 43/00 514/411 |
| 2005/0013869 A1 | 1/2005 | Chaw et al. | |
| 2005/0182044 A1 | 8/2005 | Bruinsma | |
| 2005/0272804 A1 | 12/2005 | Bruinsma | |
| 2007/0037848 A1 | 2/2007 | Masters et al. | |
| 2010/0298389 A1 | 11/2010 | Elmaleh et al. | |
| 2011/0021594 A1 | 1/2011 | Grieg et al. | |

FOREIGN PATENT DOCUMENTS

| | | | |
|---|---|---|---|
| WO | WO0166114 | 9/2001 | |
| WO | WO0248150 | 6/2002 | |
| WO | WO-03024450 A1 * | 3/2003 | ......... A61K 31/5415 |
| WO | WO03082270 | 10/2003 | |
| WO | WO2004034963 | 4/2004 | |
| WO | WO2005089746 | 9/2005 | |
| WO | WO2005123068 | 12/2005 | |
| WO | WO2010117727 | 10/2010 | |
| WO | WO2012154285 | 11/2012 | |
| WO | WO2010117727 | 10/2014 | |

OTHER PUBLICATIONS

CAS Registry, 1998 (Year: 1998).*
Cullen et al. "Brain Beta-Amyloid 42 in Mice Treated Orally with Posiphen Tartrate is Significantly Lower than in Vehicle Controls," 9$^{th}$ International Geneva/Springfield Symposium on Advances in Alzheimer Therapy; (Apr. 19, 2006).
Holloway et al. "Mechanism of Action of Posiphen in CSF of mildly Cognitive Impaired Patients," QR Pharma, Inc., Radnor, PA.
Soares et al., "Aβ Variability and Effects of Gamma Secretase Inhibition on Plasma and Cerebrospinal Fluid Levels of Aβ Peptide in Healthy Volunteers" Pfizer Global Research and Development, New London, CT.
Marutle et al. "Modulation of human neural stem cell differentiation in Alzheimer (APP23) transgenic mice by phenserine" The National Academy of Sciences of the USA; vol. 104, No. 30, pp. 12506-12511, (Jul. 24, 2007).
Brazzolotto et al., "Structural Changes Associated with Switching Activities of Human Iron Regulatory Protein 1*" The Journal of Biological Chemistry; vol. 277, No. 14, pp. 11995-12000, (2002).

(Continued)

*Primary Examiner* — Umamaheswari Ramachandran
(74) *Attorney, Agent, or Firm* — Davidson, Davidson & Kappel, LLC

(57) ABSTRACT

The invention includes an amount of (3aR)-1,3a,8-trimethyl-1,2,3,3a,8,8a-hexahydropyrrolo[2,3-b]indol-5-yl phenylcarbamate for administering to a subject and also a method of preventing or treating neurotoxicity or neurodegenerative processes in a subject in need thereof using the amount thereof.

15 Claims, 29 Drawing Sheets

Specification includes a Sequence Listing.

(56) References Cited

OTHER PUBLICATIONS

Shaw et al., "Phenserine regulates translation of β-amyloid precursor protein mRNA by a putative interleukin-1 responsive element, a target for drug development" PNAS, vol. 98, No. 13; pp. 7605-7610, (Jun. 19, 2001).
Lahiri et al. "The Experimental Alzheimer's Disease Drug Posiphen [(+)-Phenserine] Lowers Amyloid-β Peptide Levels in Cell Culture and Mice" The Journal of Pharmacology and Experimental Therapeutics, vol. 320, No. 1; pp. 386-396; (2007).
Selkoe, "Defining Molecular Targets to Prevent Alzheimer Disease" American Medical Association; pp. 192-195; (2005).
Kadir et al. "Effect of Phenserine Treatment on Brain Functional Activity and Amyloid in Alzheimer's Disease" American Neurological Association, Wiley-Liss, Inc.; pp. 621-631; (2008).
Khachaturian, "Diagnosis of Alzheimer's Disease" Arch Neurology; vol. 42, p. 1097; (Nov. 1985).
Cahill et al. "Amyloid Precursor Protein and Alpha Synuclein Translation, Implications for Iron and Inflammation in Neurodegenerative diseases" *Biochim Biophys Acta*. 1790(7): 615-628 (Jul. 2009).
Maccecchini et al. "Posiphen as a candidate drug to lower CSF amyloid precursor protein, amyloid-β peptide and τ levels: target engagement, tolerability and pharmacokinetics in humans" J Neurol Neurosurg Psychiatry; vol. 83; pp. 894-902; (2012).
Duce et al. "Iron-Export Ferroxidase Activity of β-Amyloid Precursor Protein Is Inhibited by Zinc in Alzheimer's Disease" Cell; pp. 1-10; (2010), doi: 10.1016/j.cell.2010.08.014.
Kounnas et al. " Modulation of ɤ -Secretase Reduces β-Amyloid Deposition in a Transgenic Mouse Model of Alzheimer's Disease" Neuron; pp. 1-12; (2010).
Mikkilineni et al. "The Anticholinesterase Phenserine and Its Enantiomer Posiphen as 5' Untranslated-Region-Directed Translation Blockers of the Parkinson's Alpha Synuclein Expression" Hindawi Publishing Corporation; vol. 2012, Article ID 142372.
Vent et al. "The Integrated Role of Desferrioxamine and Phenserine Targeted to an Iron-Responsive Element in the APP-mRNA 5'-Untranslated Region" Ann. N.Y. Acad. Sci. vol. 1035: pp. 34-58 (2004).
Bandyopadhyay et al. "Novel 5' Untranslated Region Directed Blockers of Iron-Regulatory Protein-1 Dependent Amyloid Precursor Protein Translation: Implications for Down Syndrome and Alzheimer's Disease" PLOS One; vol. 8, Issue 7; pp. 1-14 (2013).
Maccecchini, "Targeting Alzheimer's with Novel Therapeutics" QR Pharma, Inc. Neuroscience Network; presented by Maria Maccecchini on May 11, 2010.
Harold W Holloway et al.: "Posiphen and Analogs: Experimental Alzheimer' Agents that Reduce Amyloid-[beta] Peptide by Lowering Amyloid Precursor Protein Levels in Culture and In Vivo", 42nd Annual Winter Conference on Brain Research , Jan. 25, 2009 (Jan. 25, 2009), 42nd Annual Winter Conference on Brain Research. Abstract only.
Maccecchini et al: "Targeting Alzheimer's with Novel Therapeutics", May 11, 2010 (May 11, 2010), Neuroscience Network, <<http:l/www.qrpharma.comlpdf/2010-5-11 Alzheimers Research Today Maria Maccecchini slides.pdf>>. Last accessed Jul. 22, 2014.
Maria L. Maccecchini: "Mechanism of Action of Posiphen : From Model to Human", Jan. 26, 2011 (Jan. 26, 2011), 44nd Annual Winter Conference on Brain Research, <<http://wwwqrpharma.com/pdflWCBR Talk Jan. 2011.pdf>>. Last accessed Jul. 22, 2014.
Kadir et al: "Long-term effect of phenserine treatment in Alzheimer patients as assessed by PET and CSF biomarkers", Alzheimer's & Dementia the Journal of the Alzheimer's Association vol. 5, No. 4; p. 6.
Melo et al. Annals of the NY Academy of Sci., 1096, 1, 2007.
Maccecchini et al. (Poster presentations, Alzheimer's and Dementia, Jul. 2009, 5, 4, S1, p. 247-248).
Lahiri et al. (The J of Pharmacology and Experimental Therapeutics, 320, 1, 386-396, 2007).
Tomiyama, (The J of Biol. Chem, 271, 12, 6839-44, 1996).

Galvan, et al., "Reversal of Alzheimer's-like pathology and behavior in human APP transgenic mice by mutation of Asp664," PNAS, May 2, 2006, 103(18): pp. 7130-7135.
Nikolaev, et al., "APP binds DR6 to trigger axon pruning and neuron death via distinct caspases," Nature, Feb. 19, 2009, 457(19): pp. 981-990.
Takeda, et al., "Mechanisms ofNeuronal Death in Synucleinopathy," Journal ofBiomedicine and Biotechnology, 2006, vol. 2006, Article ID 19365, pp. 1-4.
Rogers, et al., "The alpha-synuclein 5 'untranslated region targeted translation blockers: anti-alpha synuclein efficacy of cardiac glycosides and Posiphen," .1. Neural Transm, Oct. 15, 2010, DOI 10.1007/s00702-010-0513-5.
Cho, et al., "Selective Translational Control of the Alzheimer Amyloid Precursor Protein Transcript by Iron Regulatory Protein-1," Journal ofBiological Chemistry, Oct. 8, 2010, 285(41): pp. 31217-31232.
Khachaturian, "Diagnosis of Alzheimer's Disease," Arch Neural, Nov. 1985, 42: pp. 1097-1105.
International Search Report from International WIPO Publication No. WO 2012/154285 dated Aug. 17, 2012.
Maccecchini et al. "Posiphen lowers amyloid precursor protein and amyloid beta as well as acetylcholinesterase levels in culture, animals and humans" International Conference on Alzheimer's Disease; Jul. 12, 2009 (Abstract is retrieved from http://www.qrpharma.com/pdf/ICAD_Posiphen_06-30-2009.pdf on May 19, 2012; Publication date is retrieved from http://www/qrpharma.com/pdf/WCBR_Posiphen_01%206%2009%20Poster.pdf on May. 19, 2012) abstract, Figs. 1, 3, 4, 8(2).
Greig et al. "The experimental Alzheimer drug phenserine: preclinical pharmacokinetics and pharmacodynamics" Acta Neurol Scand 2000: Supplement 176: pp. 74-84.
Office Action from corresponding Korean Patent Application No. 10-2013-7025992 dated Jul. 30, 2018.
Janas et al. "The cholinesterase inhibitor, phenserine, improves Morris water maze performance of scopolamine-treated rats" Life Sciences, Pergamon Press, Oxford, GB, vol. 76, No. 10, (Jan. 21, 2005) pp. 1073-1081.
Pike et al. "Effect of tetrahydroaminoacridine, a cholinesterase inhibitor, on cognitive performance following experimental brain injury" Journal of Neurotrauma, vol. 14, No. 12, (Dec. 1997) pp. 897-905.
David et al. "Cognitive impairments Induced by Concussive Mild Traumatic Brain Injury in Mouse are Ameliorated by Treatment with Phenserine via Multiple Non-Cholinergic and Cholinergic Mechanisms" POLS One, vol. 11, No. 6, (Jun. 2, 2016) pp. eQ156493.
International Search Report from International PCT Application No. PCT/US2016/046794 dated Feb. 23, 2017.
Greig et al., "An Overview of Phenserine Tartrate, A Novel Acetylcholinesterase Inhibitor for the Treatment of Alzheimer's Disease" Current Alzheimer Research, Bentham Science Publishers Ltd., vol. 2, pp. 281-290 (2005).
Jacobson et al., "Investigational drugs for the treatment of AD: what can we learn from negative trials?" *Alzheimer's Research & Therapy*, BioMed Central Ltd., vol. 3; No. 14; pp. 1-8 (2011).
U.S Department of Health and Human Services Food and Drug Administration Center for Drug Evaluation and Research (CDER) "Guidance for Industry Estimating the Maximum Safe Starting Dose in Initial Clinical Trials for Therapeutics in Adult Healthy Volunteers"; Jul. 6, 2005.
Maccecchini et al. "Posiphen: Experimental Alzheimer Agent that Lowers Amyloid Precursor Protein Levels in Culture and In Vivo"; Dept. Psychiatry, Institute Psychiatric Research, Indiana Univ., Indianapolis, IN: Department of Neuroscience, Center of Aging, Medical University of S. Carolina, Charleston, SC;. PowerPoint Presentation. Dated Jan. 2011.
Summons to Attend Oral Proceedings mailed on Apr. 25, 2019 in connection to European Patent Application No. 12 782 326.8.
Novak et al. (Huntington's Disease, BMJ, Jul. 3, 2010). (Year: 2010).
Laron et al. (Annu. Rev. Publ. Health 13L431-49) (Year: 1992).

(56) References Cited

OTHER PUBLICATIONS

Phukan et al. (http://neurology.thelancet.com, vol. 6, Nov. 2007). (Year: 2007).
Klein (Phenserine, Expert Opin Investig. Drugs 2007, 16(7): 1087-1097 (Year: 2007).
Enright (https://louisaenright.com/2011 /11 /), 2011 (Year: 2011).

* cited by examiner

Fig. 7B

| | | |
|---|---|---|
| Human APP mRNA (46) | GGGGGCCCCGGAGAGACGGCGGCGGT*GGCGGCGCGGGCAGAGACAAGGACGCGGCGGA*TC | AUG (-43) |
| Mouse APP mRNA (33) | GGGGCCACCGGAGAGACGGCGGCGGCGGGCG----CGGACACAGCCAGGGCGCGGCGGATC | AUG (-45) |
| Rhesus APP (137) | GGGTCCCCCGGAGAGACGGCGGCGGCGGTGGCG---CGGGCAGAGACAAGGACGCGGCGGATC | AUG (-43) |
| Human L-Chain (3) | GTTCGGCGGTCCCCGGGGTCTCGTCTCTTGCTTCAACAGTGTTTGGACGGAAGAGATC | AUG (-139) |
| Human H-Chain (5) | TCTTCGCCGAGAGTCGTCGGGGTTTCCTGCTTCAACAGTGCTTGGACGGAAGCCGGC | AUG (-149) |
| Consensus | G-------G------C-----CA----G--CG--GG--CG--C----C | |

| | |
|---|---|
| HumanAPP mRNA | SEQ ID NO:1 |
| Mouse APP mRNA | SEQ ID NO:2 |
| Rhesus APP | SEQ ID NO:3 |
| Human L-chain | SEQ ID NO:4 |
| Human H-chain | SEQ ID NO:5 |
| Consensus | SEQ ID NO:6 |

Fig. 8
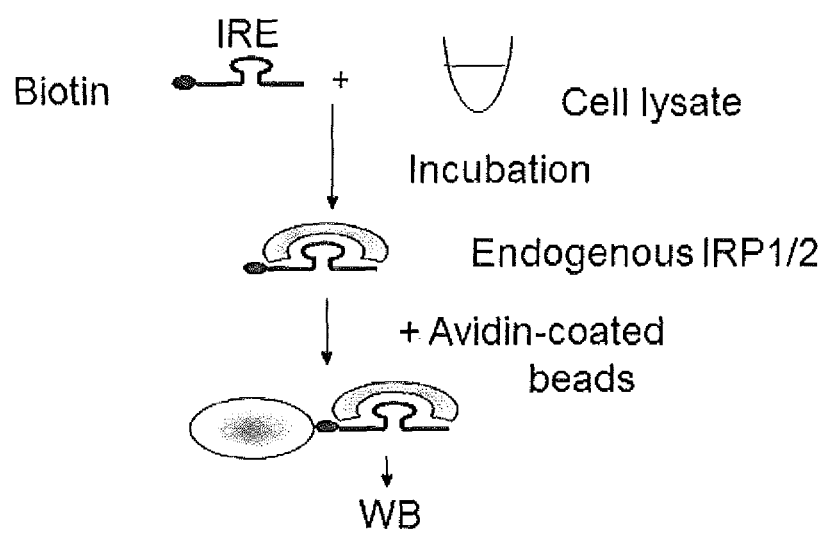
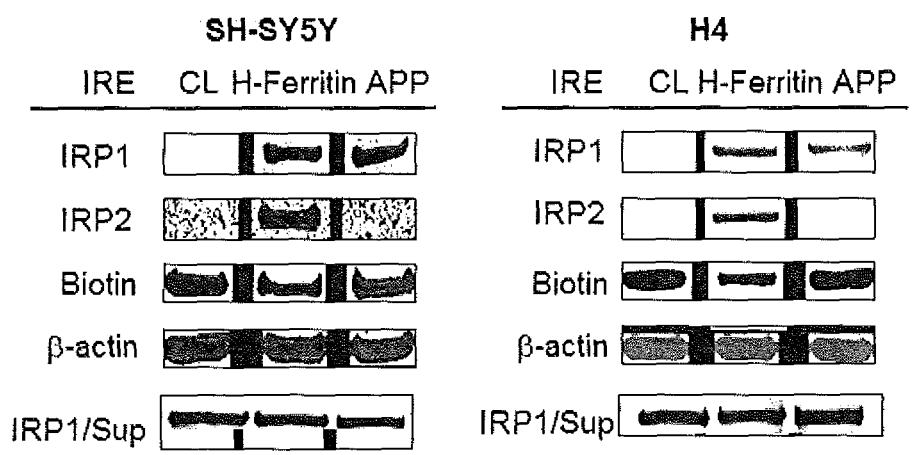

Fig. 9B

| Consensus Loop (from IRE stemloop) | | | CAGTGN | |
|---|---|---|---|---|
| H-chain | 5' | 53 | CGGGGTTCCTGCTTCAACAGTGCTTGGACGGAACCCGGCGCTCGT | 3' 99 |
| L-chain | 5' | 21 | GTCTGTCTCTTGCTTCAACAGTGTTTGGACGGAACAGATCCGGGA | 3' 67 |
| ASYN | 5' | 1 | GGAGTGGCCATTCGACGACAGTGTGGTGTAAAGGAATTCATTAGCC | 3' 50 |
| APP | 5' | 64 | CGGCGGTGGGCGGGCAGGACAAGGACGCGGGCGATCCCACTC | 3' 103 |

| | | |
|---|---|---|
| ASYN IRE Loop (L-ferritin IRE Homology) | CAGTGT | |
| APP IRE Loop (H-ferritin IRE Homology) | CAGAGCAAGGACG | 10 |

H-chain      SEQ ID NO:7

L-chain      SEQ ID NO:8

ASYN      SEQ ID NO:9

APP      SEQ ID NO:10

APP IRE loop      SEQ ID NO:11

| | |
|---|---|
| H sapiens | SEQ ID NO:12 |
| P. troglodytes | SEQ ID NO:12 |
| M. musculus | SEQ ID NO:13 |
| R. novergicus | SEQ ID NO:14 |
| B. taurus | SEQ ID NO:15 |
| C. lupus | SEQ ID NO:16 |
| G. gallus | SEQ ID NO:17 |
| Ferritin H-chain | SEQ ID NO:18 |
| Ferritin L-chain | SEQ ID NO:19 |
| APP | SEQ ID NO:20 |

Fig. 12
B. RNA Secondary Structures
Evolutionary α-Synuclein RNA IRE Structures
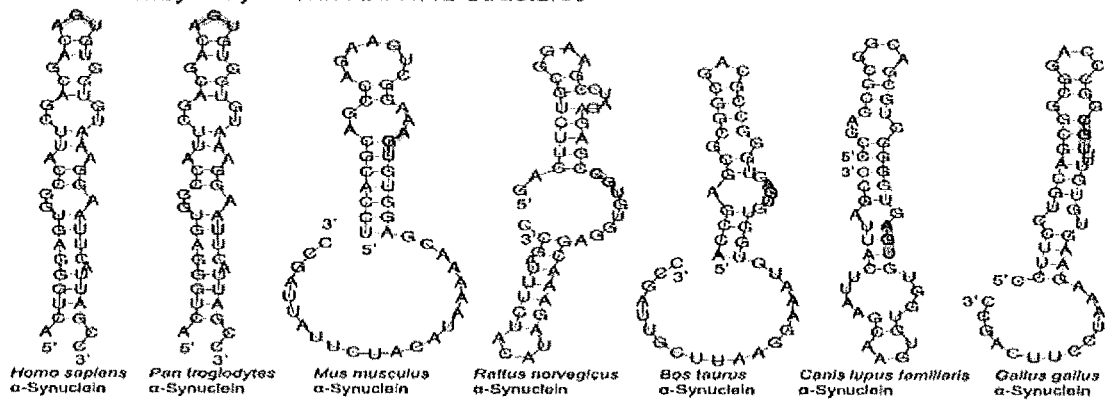
Known IREs in Human Genes
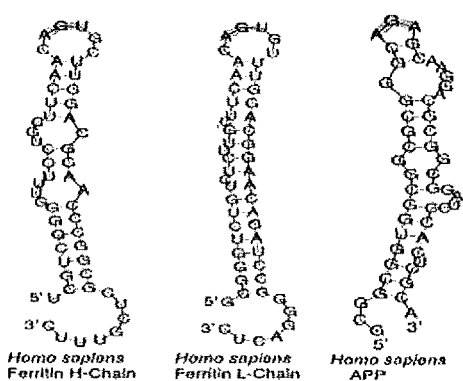
C. Comparison of Human Synuclein Homologs
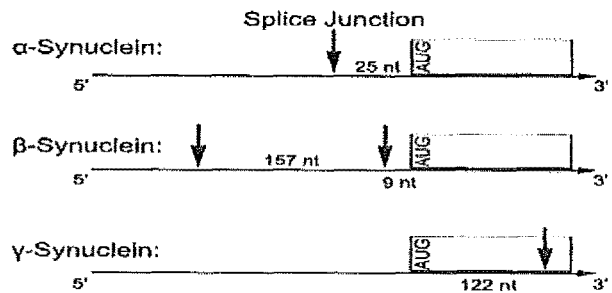

| | |
|---|---|
| H. sapiens | SEQ ID NO:21 |
| G. gorilla | SEQ ID NO:22 |
| P. troglodytes | SEQ ID NO:23 |
| M. fascicularis | SEQ ID NO:24 |
| light-chain ferritin | |
| | SEQ ID NO:25 |
| heavy-chain ferritin | |
| | SEQ ID NO:26 |
| APP | SEQ ID NO:27 |
| B. Taurus | SEQ ID NO:28 |
| O. aries | SEQ ID NO:29 |
| R. norvegicus | SEQ ID NO:30 |
| M. musculus | SEQ ID NO:31 |
| beta-actin | SEQ ID NO:32 |

Fig. 14

| Protein | Disease | IRE Stem | Inhibited by Posiphen | | |
|---|---|---|---|---|---|
| | | | in vitro | mouse | humans |
| APP | AD | X | X | X | X |
| SNCA | PD | X | X | X | X |
| Prions | CJ | X | X | X | nd |
| SOD | ALS | X | nd | nd | nd |
| HTT | HT | tbd | nd | nd | nd |
| Tau | many | X | tbd | tbd | X |

Fig. 17
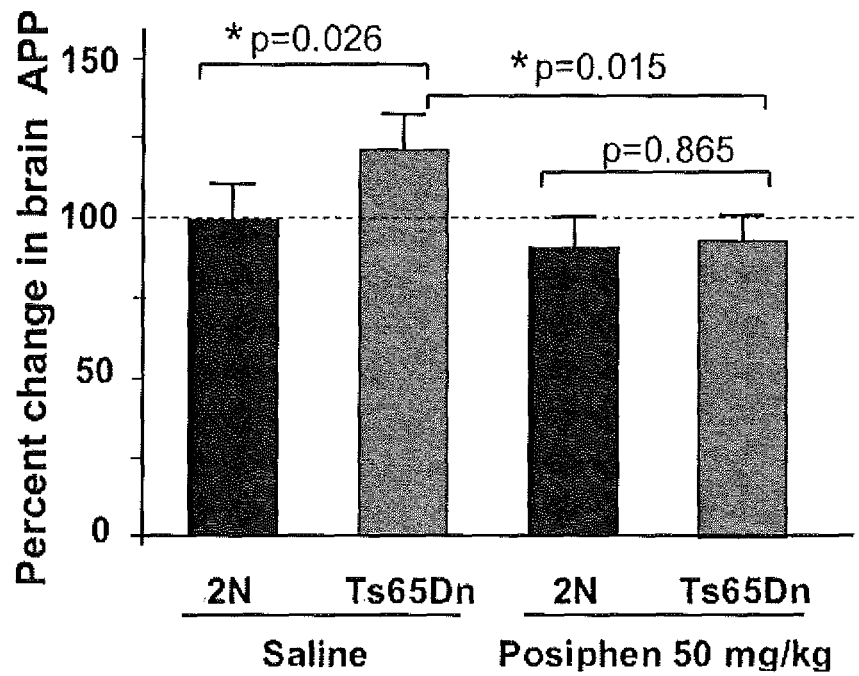
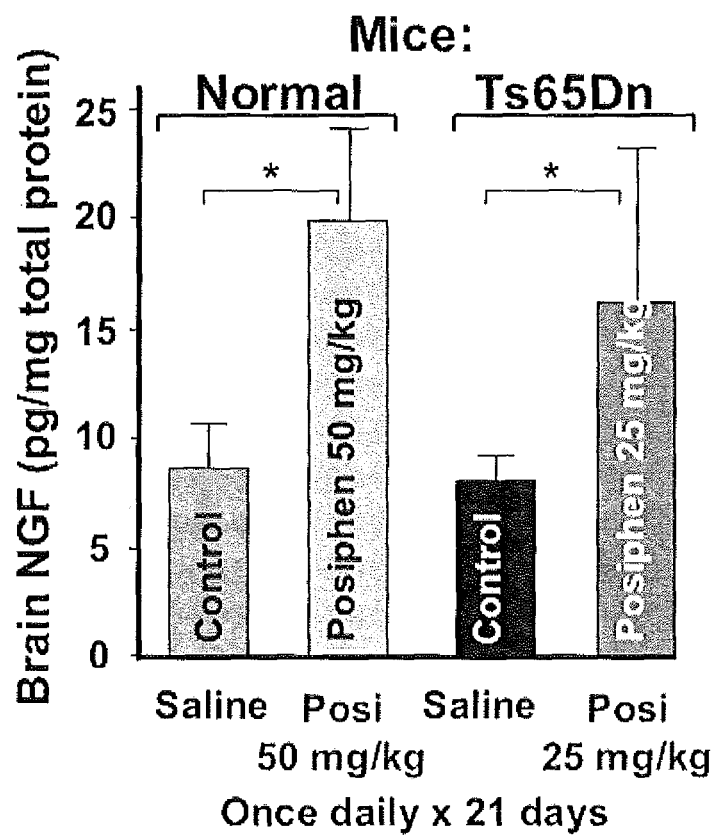

Fig. 19

| Inhibition of | Compound (1) or Posiphen | Compound (2) or $N^1$-norposiphen | Compound (3) or $N^8$-norposiphen | Compound (4) or $N^1,N^8$-norposiphen |
|---|---|---|---|---|
| APP | + | + | + | + |
| Aβ | + | + | + | + |
| APPneo/C31 | + | 0 | 0 | +/- |
| alpha-synuclein | + | tbd | tbd | + |
| 5'UTR$^{APP}$ Luciferase | + | tbd | tbd | + |
| AChE | 0 | + | 0 | +/- |
| BChE | 0 | 0 | 0 | 0 |

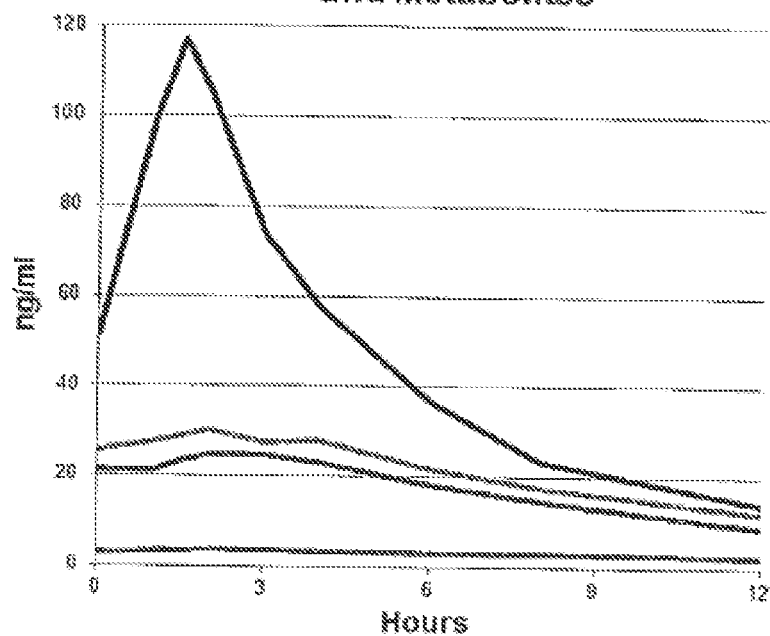
Fig. 22A Human Plasma Levels of Posiphen and Metabolites
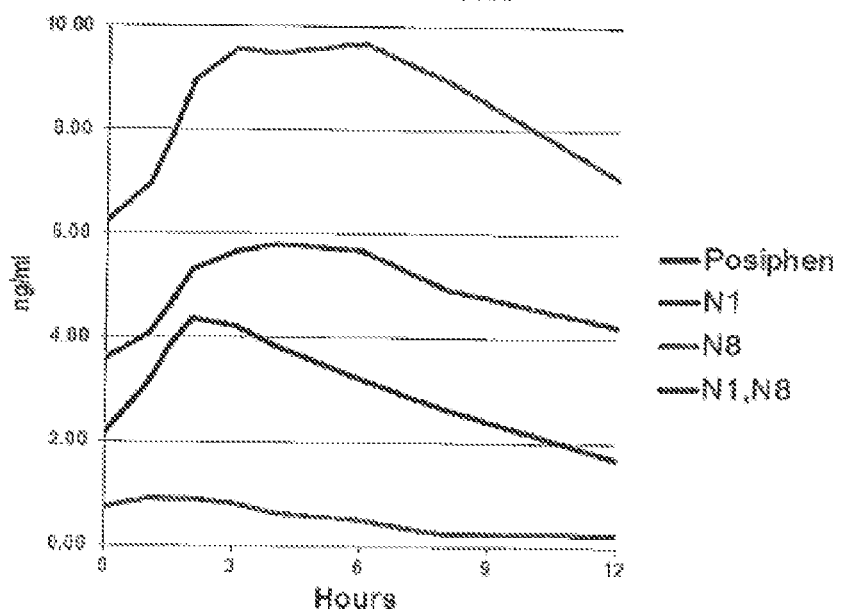
Fig. 22B Human CSF Levels of Posiphen and Metabolites

Fig. 23

| Human Biomarker | CSF | Assay |
|---|---|---|
| sAPP α | -40% | MSD |
| | -33% | AlphaLisa |
| sAPP β | -45% | MSD |
| | -45% | AlphaLisa |
| Tau | -40% | AlphaLisa |
| | -38% | Innogenetics |
| pTau | -31% | Innogenetics |
| Aβ42 | ~ 0 | Innogenetics |

| Ratios | MCI Day 0 | MCI Day 11 | non AD |
|---|---|---|---|
| Tau/Aβ 42 | 0.56 | 0.35 | 0.31 |

Fig. 26

| Analyte | Parameter | Human Plasma | | Dog Plasma | | Ratio Dog Mean / Human Mean |
|---|---|---|---|---|---|---|
| | | Mean | SD | Mean | SD | |
| Posiphen | Cmax | 118.5 | 24.8 | 741.3 | 188.4 | 6.3 |
| | $AUC_{0-last}$ | 570.0 | 235.4 | 1575.6 | 286.0 | 2.8 |
| $N^1$-Norposiphen | Cmax | 25.6 | 6.7 | 770.8 | 46.2 | 30.1 |
| | $AUC_{0-last}$ | 214.4 | 77.1 | 2467.3 | 121.4 | 11.5 |
| $N^8$-Norposiphen | Cmax | 31.0 | 7.1 | 35.2 | 15.7 | 1.1 |
| | $AUC_{0-last}$ | 261.3 | 91.3 | 104.0 | 34.8 | 0.4 |
| $N^1,N^8$ Bisnorposiphen | Cmax | 3.8 | 1.2 | 46.8 | 12.8 | 12.5 |
| | $AUC_{0-last}$ | 36.9 | 12.5 | 241.9 | 44.1 | 6.6 |

| Analyte | Human Plasma $C_{max}$ | | Rat Plasma Avg Conc* | | Ratio Rat Mean Plasma Conc / Human Mean $C_{max}$ |
|---|---|---|---|---|---|
| | Mean | SD | Mean | SD | |
| Posiphen | 118.5 | 24.8 | 2485 | 659 | 21.0 |
| $N^1$ Norposiphen | 25.6 | 6.7 | 161 | 78.8 | 6.3 |
| $N^8$ Norposiphen | 31.0 | 7.1 | 167 | 91.6 | 5.4 |
| $N^1,N^8$ Bisnorposiphen | 3.8 | 1.2 | 17.0 | 7.04 | 4.5 |

| Analyte | Dog Plasma Mean $AUC_{0-last}$ | Dog Plasma SD $AUC_{0-last}$ | Dog Plasma %CV $AUC_{0-last}$ | Dog Plasma Mean Cmax | Dog Plasma SD Cmax | Dog Plasma %CV Cmax |
|---|---|---|---|---|---|---|
| Posiphen | 1575.6 | 286.0 | 18.1% | 741.3 | 188.4 | 25.4% |
| $N^1$-norposiphen | 2467.3 | 121.4 | 4.9% | 770.8 | 46.2 | 6.0% |
| $N^8$-norposiphen | 104.0 | 34.8 | 33.5% | 35.2 | 15.7 | 44.6% |
| $N^1,N^8$-norposiphen | 241.9 | 44.1 | 18.2% | 46.8 | 12.8 | 27.3% |

(3AR)-1,3A,8-TRIMETHYL-1,2,3,3A,8,8A-HEXAHYDROPYRROLO[2,3-B]INDOL-5-YL PHENYLCARBAMATE AND METHODS OF TREATING OR PREVENTING NEURODEGENERATION

BACKGROUND OF THE INVENTION

Neurotoxic Precipitating Fibrillar Proteins

Neurodegenerative diseases generally affect abstract thinking, skilled movements, emotional feelings, cognition, memory and other abilities. Despite differences in clinical symptoms and disease progression, disorders from this group share key common features: most of them have both sporadic and inherited origins, all of them appear later in life (usually after the fourth or fifth decade of the subject's life), and their pathology is characterized by neuronal loss and synaptic abnormalities. Until recently, no common molecular mechanism had been identified among these diseases. However, various neurodegenerative diseases, such as Alzheimer's disease (AD), Parkinson's disease (PD), Huntington's disease (HD), transmissible spongiform encephalopathies (TSEs), and amyotrophic lateral sclerosis (ALS), have been shown to share a common cause and pathological mechanism—the misfolding, aggregation and accumulation of proteins in the brain, resulting in neuronal apoptosis. The hallmark feature of conformational disorders is that a particular protein folds into a stable alternative conformation, which in most cases results in its aggregation and accumulation in tissues as fibrillar deposits. These deposits have similar morphological, structural and staining characteristics (FIGS. 3 and 4). Multidisciplinary studies strongly support this shared cause and pathological mechanism, suggesting that there may be a common therapy for these devastating disorders.

Mutations in the genes that encode the protein components of fibrillar aggregates are genetically associated with the inherited forms of all neurodegenerative diseases. The familial forms usually have an earlier onset and greater severity than sporadic cases and are also associated with a greater amount of protein aggregates (Soto, 2003, Nature Rev. 4:49).

Neurotoxic aggregating proteins have not only a common aggregating pathway, but also common regulatory pathways for their transcription and translation. While their transcription is activated by copper and/or zinc ions (Bush et al., 2003, Proc. Natl. Acad. Sci. U.S.A. 100(20):11193-94), their translation is upregulated by iron and down-regulated by iron regulatory protein 1 (IRP1) (FIG. 6A). Specifically, their mRNAs are regulated via the 5'-untranslated region (5'UTR) of their transcript, which folds into a unique RNA stem loop with a CAGUGN apical loop similar to that encoded in the canonical iron-responsive element (IRE) of L- & H-ferritin mRNAs (FIGS. 7A, 7B, 9B and 12). IRP1 binds to this IRE stem look and inhibits the translation of the mRNA by the ribosome (Cho et al., 2010, J. Biol. Chem. 285(40:31217; FIG. 13). Binding assays have been developed based on these protein interactions (FIG. 8).

Examples of neurotoxic aggregating proteins are APP (amyloid precursor protein), Aβ (amyloid-β peptide, a fragment of APP), SOD (super oxide dismutase) proteins, Tau, alpha-synuclein (SNCA), transmissible spongiform encephalopathy (TSE) prions, and huntingtin (HTT).

In humans, alpha-synuclein is encoded by the SNCA gene (FIG. 11). An alpha-synuclein fragment, known as the non-Aβ component (NAC) of Alzheimer's disease amyloid and originally found in an amyloid-enriched fraction, is shown to be a fragment of its precursor protein, NACP (now referred to as human alpha-synuclein).

Even though tau is not a member of the iron regulated neurotoxic protein family, it is overexpressed and aggregates in a number of tauopathies. Conditions in which neurofibrillary tangles are commonly observed include: Alzheimer's disease, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), Tangle-predominant dementia, with NFTs similar to AD, but without plaques. Tau deposits tend to appear in the very old, Picks disease and a number of other neuropathies. Tau's fibrillary tangles are found in most neurodegenerative disorders.

Transmissible spongiform encephalopathies (TSEs, collectively known as prion diseases) are a group of progressive conditions that affect the brain and nervous system of mammals, and include devastating diseases as bovine spongiform encephalopathy (BSE, also known as "mad cow disease") in cattle, and classic Creutzfeldt-Jakob disease, new variant Creutzfeldt-Jakob disease (nvCJD, a human disorder related to mad cow disease), Gerstmann-Sträussler-Scheinker syndrome, fatal familial insomnia and kuru (CJD) in humans. Mental and physical abilities deteriorate in the afflicted patients, and myriad tiny holes appear in the cortex, causing it to appear like a sponge (hence 'spongiform') when brain tissue obtained at autopsy is examined under a microscope. The disorders cause impairment of brain function, including memory changes, personality changes and problems with movement that worsen over time.

Unlike other kinds of infectious disease by microbes, the infectious agent in TSEs is thought to be a specific protein called prion protein. Misshaped prion proteins carry the disease between individuals and cause deterioration of the brain. TSEs are unique diseases, in that their etiology may be genetic, sporadic or infectious via ingestion of infected foodstuffs and via iatrogenic means (e.g. blood transfusion). Most TSEs are sporadic and occur in an animal with no prion protein mutation. Inherited TSE occurs in animals carrying a rare mutant prion allele, which expresses prion proteins that contort by themselves into the disease-causing conformation.

The degenerative tissue damage caused by human prion diseases (Creutzfeldt-Jakob disease, Gerstmann-Sträussler-Scheinker syndrome, and kuru) is characterised by four features: spongiform change, neuronal loss, astrocytosis and amyloid plaque formation. These neuropathological features have formed the basis of the histological diagnosis of human prion diseases for many years, although it was recognized that these changes are enormously variable both from case to case and within the central nervous system in individual cases.

Transmissible spongiform encephalopathies encompass the following diseases (including natural host and prion name): scrapie (sheep and goats; scrapie prion); transmissible mink encephalopathy (TME) (mink; TME prion); chronic wasting disease (CWD) (elk, white-tailed deer, mule deer and red deer; CWD prion); bovine spongiform encephalopathy (BSE) commonly known as "mad cow disease" (cattle; BSE prion); feline spongiform encephalopathy (FSE) (cats; FSE prion); Exotic ungulate encephalopathy (EUE) (nyala and greater kudu; EUE prion); kuru (human; Kum prion); Creutzfeldt-Jakob disease (CJD) or Variant Creutzfeldt-Jakob disease (vCJD, nvCJD) (human; CJD and vCJD prions); Gerstmann-Sträussler-Scheinker syndrome (GSS) (human; GSS prion); and fatal familial insomnia (FFI) (human; FFI prion).

Alzheimer's Disease

Alzheimer's disease (AD) is the most common progressive dementia associated with aging. The cholinergic system is the earliest and most profoundly affected neurotransmitter system in AD, with substantial losses in the forebrain, cortex and hippocampus, which are critical in the acquisition, processing and storage of memories (Terry et al., 1991, Ann. Neural. 30:572-80; Giacobini, In "Alzheimer's Disease: Molecular Biology to Therapy"; Becker & Giacobini, Eds.; Birkhauser: Boston, 1997; pp 188-204; Becker et al., In "Alzheimer's Disease: from Molecular Biology to Therapy"; Becker & Giacobini, Eds.; Birkhauser: Boston, 1997; pp 257-66).

The major neuropathological hallmarks of AD are β-amyloid plaques, neurofibrillary tangles, and synaptic loss (Khachaturian, 1985, Arch. Neural. 42:1095-1105; FIG. 1). In particular, amyloid-β precursor protein (APP) is cleaved into a number of toxic peptides, one of them being amyloid-β (Aβ): a hydrophobic, neurotoxic self-aggregating 40 to 42 amino-acid peptide that accumulates preferentially within senile plaques in the brain. Other peptides are also cleaved from the N-terminus and C-terminus end of APPs. These peptides attack multiple pathways of neuronal cell life, leading to synaptic loss and nerve cell death. This sequence of events induces neuroinflammation and leads to cognitive impairment and neurodegeneration (FIG. 2).

In an original hypothesis for AD treatment, inhibition of the accumulation of Aβ in the brain could positively affect the course of AD. Recently, this hypothesis has been expanded by recognizing that APP in the absence of trophic factors is shed from the surface of neuronal cells and processed into an amino terminal fragment (N-APP). This fragment binds to DR6 receptors and induces nerve cell death (Nicolaev et al., 2009, Nature 457:981-90). Furthermore, C31 (another factor cleaved from the C-terminus end of APP) has been found to cause nerve cell degeneration and death in tissue culture cells and in transgenic mice (Galvan et al., 2006, PNAS 103(18):7130-35). Overexpression of C31 has been also shown to lead to neuronal degeneration without Aβ toxicity and plaque deposition. In all three cases (cell death triggered by N-APP, Aβ and/or C31 accumulation), reducing APP synthesis could be beneficial to the preservation of brain cells, by reducing the formation of neurotoxic plaque through the Aβ pathway and by inhibiting the formation of nerve cell-killing toxic N-terminus and C-terminus fragments.

Current Drugs on Market—Symptomatic Compounds

Current AD therapeutic drugs on the market include improving cognitive processes by increasing the levels of acetylcholine. The agents that have demonstrated the greatest promise in preclinical development are cholinesterase inhibitors and cholinomimetics. The best characterized cholinesterase is acetylcholinesterase (AChE; EC 3.1.1.7; Soreq et al., "Human Cholinesterases and Anticholinesterases"; Academic Press: New York, 1993). AChE selective inhibitors are used in treatment of AD to amplify the action of acetylcholine (ACh) at remaining cholinergic synapses within the AD brain. In fact, various AChE inhibitors (such as donepezil, galantamine and rivastigmine) and a NMDA glutamate receptor blocker (memantine) are the only FDA approved drugs for AD, primarily providing symptomatic relief to the patient.

Current Compounds in Development—Disease Modifying Compounds

A number of potential Alzheimer's DMDs are in Phase II or Phase III clinical trials. Two players (Elan-Wyeth-J&J, and Eli Lilly) lead the way as the frontrunners with a monoclonal and a humanized antibody against. Aβ, respectively, in Phase III clinical trials. Compounds currently in Phase I or entering Phase II clinical trials include Rinat/Pfizer's humanized monoclonal antibody, Prana's chelator and QR Pharma's Posiphen®. Recently various compounds in Phase II/III failed in the clinic: Lilly's γ-secretase inhibitor, Medivation/Pfizer's Dimebon®, an antihistamine, TransTech/Pfizer's RAGE®, and CoMentis/Astella's antibody.

Posiphen®

Posiphen® (also known as (3aR)-1,3a,8-trimethyl-1,2,3, 3a,8,8a-hexahydropyrrolo[2,3-b]indol-5-yl phenylcarbamate; Compound (1) hereafter) is a novel AD drug candidate that is distinct from the AD drugs currently available as well as from the AD drugs currently in development. Compound (1) optimally matches AChE inhibitory activity with APP/Aβ lowering action. This dual-mechanism of action allows for disease modification (by substantially lowering brain amyloid levels) and immediate symptomatic improvement (by inhibiting acetyl cholinesterase).

Compound (1) is a small orally active compound that has high blood brain barrier permeability (7:1) and lowers amyloid-β precursor protein (APP) levels. In cell cultures, Compound (1) was shown to inhibit APP synthesis and reduce Aβ formation. The AChE inhibition observed for Compound (1) was found to reside on the $N^1$-desmethyl metabolite of Compound (1). Because of this characteristic, Compound (1) has slow onset acetylcholinesterase inhibitory action. Compound (1) and its metabolites enter the brain readily, with a 2- to 2.5-time longer half-life in brain than in plasma, leading to prolonged efficacy. Compound (1) has been shown to have an excellent toxicology profile and a much better safety profile than traditional AChE inhibitors in animals.

Posiphen® also inhibits the translation of other neurodegenerative aggregating proteins such as alpha-synuclein, prions and super oxide dismutase due to its effect on IRP1/IRE in the 5'UTR stem looks structure of their mRNAs. (FIGS. 5, 6, 9A, and 10).

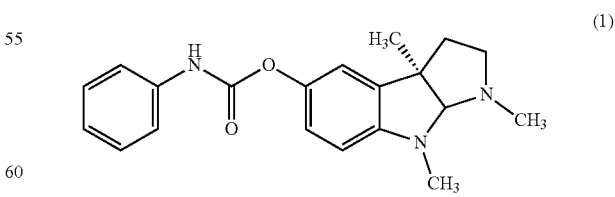

(1)

There is a need in the art to identify novel formulations and dosing regimens that allow the administration of Compound (1) or a salt thereof to effectively treat neurodegenerative diseases, such as but not limited to AD, in a subject. The present invention fills this need.

BRIEF SUMMARY OF THE INVENTION

The invention includes an amount of (3aR)-1,3a,8-trimethyl-1,2,3,3a,8,8a-hexahydropyrrolo[2,3 b]indol-5-yl phenylcarbamate (Compound (1)) or a salt thereof, wherein administering the amount to a subject results in a peak plasma circulating level of Compound (1) ranging from about 10 ng/mL to about 160 ng/ml in the subject.

In one embodiment, the peak plasma circulating level ranges from about 80 ng/mL to about 160 ng/ml in the subject. In another embodiment, the peak plasma circulating level is reached within about 6 hours after the administering. In yet another embodiment, the peak plasma circulating level is reached within about 3 hours after the administering. In yet another embodiment, the plasma circulating level of Compound (1) is equal to or greater than about 20 ng/mL for at least 12 hours after the administering. In yet another embodiment, the plasma circulating level of Compound (1) is equal to or greater than about 20 ng/mL for at least 9 hours after the administering. In yet another embodiment, the administering results in a peak plasma concentration of Compound (2) ranging from about 15% to about 30% of the peak plasma concentration of Compound (1) in the subject. In yet another embodiment, the administering results in a peak plasma concentration of Compound (3) ranging from about 15% to about 30% of the peak plasma concentration of Compound (1) in the subject. In yet another embodiment, the administering results in a peak plasma concentration of Compound (4) ranging from about 1% to about 9% of the peak plasma concentration of Compound (1) in the subject. In yet another embodiment, the administering results in a steady state plasma concentration of Compound (1) of at least about 100 ng/ml in the subject. In yet another embodiment, the administering results in a steady state plasma concentration of Compound (2) of at least about 10 ng/ml in the subject. In yet another embodiment, the administering results in a steady state plasma concentration of Compound (3) of at least about 10 ng/ml in the subject. In yet another embodiment, the administering results in a steady state plasma concentration of Compound (4) of at least about 3 ng/ml in the subject. In yet another embodiment, the administering results in a brain level of Compound (1) that ranges from about 4 to about 10 times the plasma level of Compound (1) in the subject. In yet another embodiment, the brain level of Compound (2) ranges from about 15% to about 150% of the brain level of Compound (1) in the subject. In yet another embodiment, the brain level of Compound (3) ranges from about 15% to about 150% of the brain level of Compound (1) in the subject. In yet another embodiment, the brain level of Compound (4) is lower than the brain level of Compound (2) or Compound (3) in the subject. In yet another embodiment, the subject is a human.

The invention also includes a method of inhibiting production of a neurotoxic aggregating protein in a subject. The method comprises administering to the subject a pharmaceutical composition comprising a pharmaceutically acceptable carrier and an amount of Compound (1) or a salt thereof, wherein administering the composition to the subject results in a peak plasma circulating level of Compound (1) ranging from about 10 ng/ml to about 160 mg/ml in the subject, whereby production of the neurotoxic aggregating protein in the subject is inhibited.

In one embodiment, the neurotoxic aggregating protein is selected from the group consisting of APP, Aβ, SOD, Tau, alpha-synuclein (SNCA), NAC, TSE and HTT. In another embodiment, the administering results in a reduction equal to or greater than about 25% in a cerebrospinal fluid marker selected from the group consisting of sAPP α, sAPP β, Tau and pTau in the subject. In yet another embodiment, the administering results in a reduction equal to or greater than about 30% in a cerebrospinal fluid marker selected from the group consisting of sAPP α, sAPP β, Tau and pTau in the subject.

The invention also includes a method of treating dementia in a subject. The method comprises administering to the subject a pharmaceutical composition comprising a pharmaceutically acceptable carrier and an amount of Compound (1) or a salt thereof, wherein administering the composition to the subject results in a peak plasma circulating level of Compound (1) ranging from about 10 ng/mL to about 160 ng/ml in the subject, whereby the dementia in the subject is treated.

In one embodiment, the dementia is Alzheimer's disease. In another embodiment, the dementia is selected from the group consisting of Parkinson's disease, Huntington's disease, Prion's disease, Amyloid Lateral Sclerosis and a tauopathy. In yet another embodiment, the administering results in a reduction equal to or greater than about 25% in a cerebrospinal fluid marker selected from the group consisting of sAPP α, sAPP β, Tau and pTau in the subject. In yet another embodiment, the administering results in a reduction equal to or greater than about 30% in a cerebrospinal fluid marker selected from the group consisting of sAPP α, sAPP β, Tau and pTau in the subject.

In one embodiment, the peak plasma circulating level ranges from about 80 ng/mL to about 160 ng/ml in the subject. In another embodiment, the peak plasma circulating level is reached within about 6 hours after the administering. In yet another embodiment, the peak plasma circulating level is reached within about 3 hours after the administering. In yet another embodiment, the plasma circulating level of Compound (1) is equal to or greater than about 20 ng/mL for at least 12 hours after the administering. In yet another embodiment, the plasma circulating level of Compound (1) is equal to or greater than about 20 ng/mL for at least 9 hours after the administering. In yet another embodiment, the administering results in a peak plasma concentration of Compound (2) ranging from about 15% to about 30% of the peak plasma concentration of Compound (1) in the subject. In yet another embodiment, the administering results in a peak plasma concentration of Compound (3) ranging from about 15% to about 30% of the peak plasma concentration of Compound (1) in the subject. In yet another embodiment, the administering results in a peak plasma concentration of Compound (4) ranging from about 1% to about 9% of the peak plasma concentration of Compound (1) in the subject. In yet another embodiment, the administering results in a steady state plasma concentration of Compound (1) of at least about 100 ng/ml in the subject. In yet another embodiment, the administering results in a steady state plasma concentration of Compound (2) of at least about 10 ng/ml in the subject. In yet another embodiment, the administering results in a steady state plasma concentration of Compound (3) of at least about 10 ng/ml in the subject. In yet another embodiment, the administering results in a steady state plasma concentration of Compound (4) of at least about 3 ng/ml in the subject. In yet another embodiment, the administering results in a brain level of Compound (1) that ranges from about 4 to about 10 times the plasma level of Compound (1) in the subject. In yet another embodiment, the brain level of Compound (2) ranges from about 15% to about 150% of the brain level of Compound (1) in the subject. In yet another embodiment, the brain level of Compound (3) ranges from about 15% to about 150% of the brain level of Compound (1) in the subject. In yet another embodiment, the brain level of Compound (4) is lower than the brain level of Compound (2) or Compound (3) in the subject. In yet another embodiment, the subject is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 5, comprising FIG. 5A: 10 min $^{35}$S incorporation into APP, in SH-SY-5Y human neuroblastoma cells. FIG. 5B: newly synthesized total protein. FIG. 5C: newly synthesized APP. FIG. 5D: APP mRNA.

FIG. 6, comprising FIG. 6A is a scheme illustrating the translational regulation of iron and IRP1 5'-UTR of APP mRNA. FIG. 6B is a scheme illustrating the mechanism of action of Compound (1) on 5'UTR of APP mRNA.

FIG. 7, comprising FIGS. 7A-7B, illustrates 5' UTR sequence homology of APP in mammals. HumanAPP mRNA, SEQ ID NO:1; Mouse APP mRNA, SEQ ID NO:2; Rhesus APP, SEQ ID NO:3; Human L-chain, SEQ ID NO:4; Human H-chain, SEQ ID NO:5; Consensus, SEQ ID NO:6.

FIG. 8 is a scheme illustrating the IRP/IRE binding assay.

FIG. 9, comprising FIGS. 9A-9B, illustrates the concentration-dependent inhibition of APP and alpha-synuclein translation by Compound (1). H-chain, SEQ ID NO:7; L-chain, SEQ ID NO:8; ASYN, SEQ ID NO:9; APP, SEQ ID NO:10; APP IRE loop, SEQ ID NO:11.

FIG. 12 is a scheme illustrating the 5' UTR stem loop homology of SNCA in mammals and birds.

FIG. 14 is a table illustrating the 5' UTR sequence homology and Posiphen® inhibition across neurotoxic fibrillar proteins.

FIG. 17 is a series of graphs illustrating effects of Compound (1) in Ts65Dn mouse model of Down Syndrome. Compound (1) lowered APP levels by 30% in brain of trisomy Down Syndrome mice (to control—non-DS brain levels), and achieved a 10:1 ratio of brain to plasma levels. NGF levels were elevated in brain, suggesting a potential therapeutic use. Brain AChE levels were significantly lowered (50% at Compound (1) 50 mg/kg), suggesting that administration of Compound (1) provides anticholinergic activity.

$N^1$-nor-Posiphen [Compound (2) or (3aR)-3a,8-dimethyl-1,2,3,3a,8,8a-hexahydropyrrolo[2,3-b]indol-5-yl phenylcarbamate], $N^8$-nor-Posiphen [Compound (3) or (3aR)-1,3a-dimethyl-1,2,3,3a,8,8a-hexahydropyrrolo[2,3-b]indol-5-yl phenylcarbamate], or $N^1,N^8$-nor-Posiphen [Compound (4) or (3aR)-3a-methyl-1,2,3,3a,8,8a-hexahydropyrrolo[2,3-b]indol-5-yl phenylcarbamate].

FIG. 19 is a table illustrating the effects of Compound (1) and selected metabolites on molecular markers. Compound (1) is metabolized in the liver into three major compounds: Compounds (2), (3) and (4).

Figure 1:
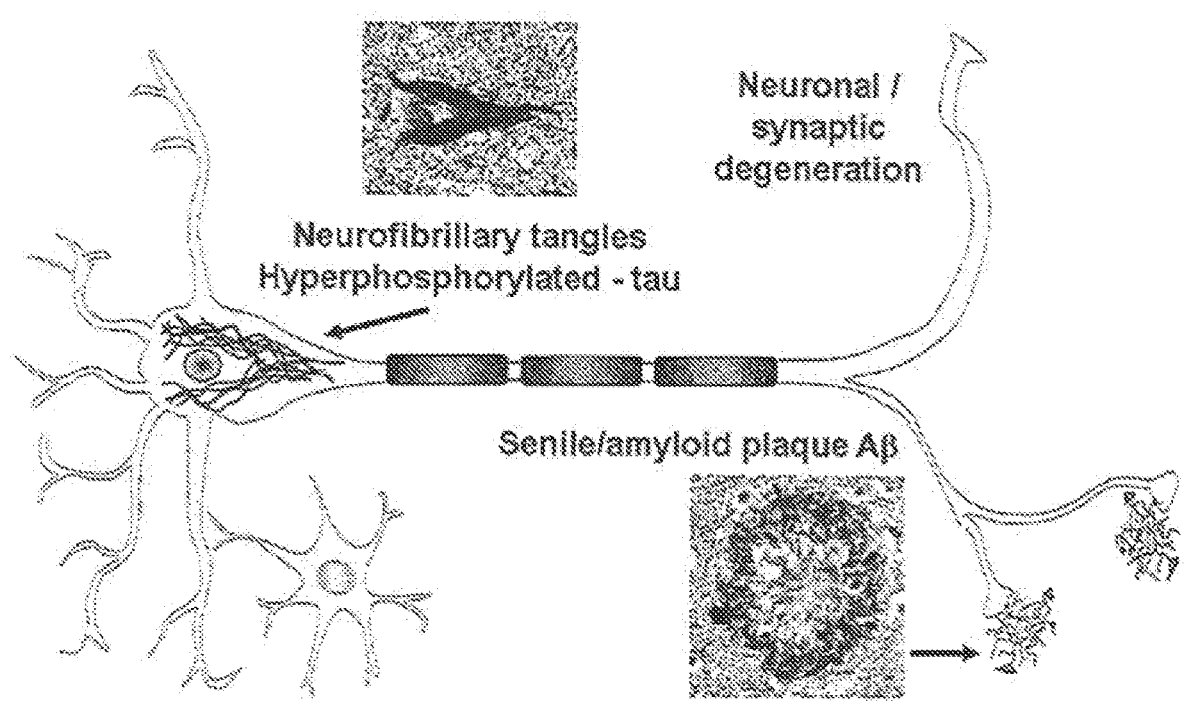
FIG. 1 is a scheme illustrating the correlation between Alzheimer's disease, and (a) senile plaque (amyloid-β peptide), (b) neurofibrillary tangles (hyperphosphorylated tau) and (c) synaptic and neuronal degeneration.
Figure 2:
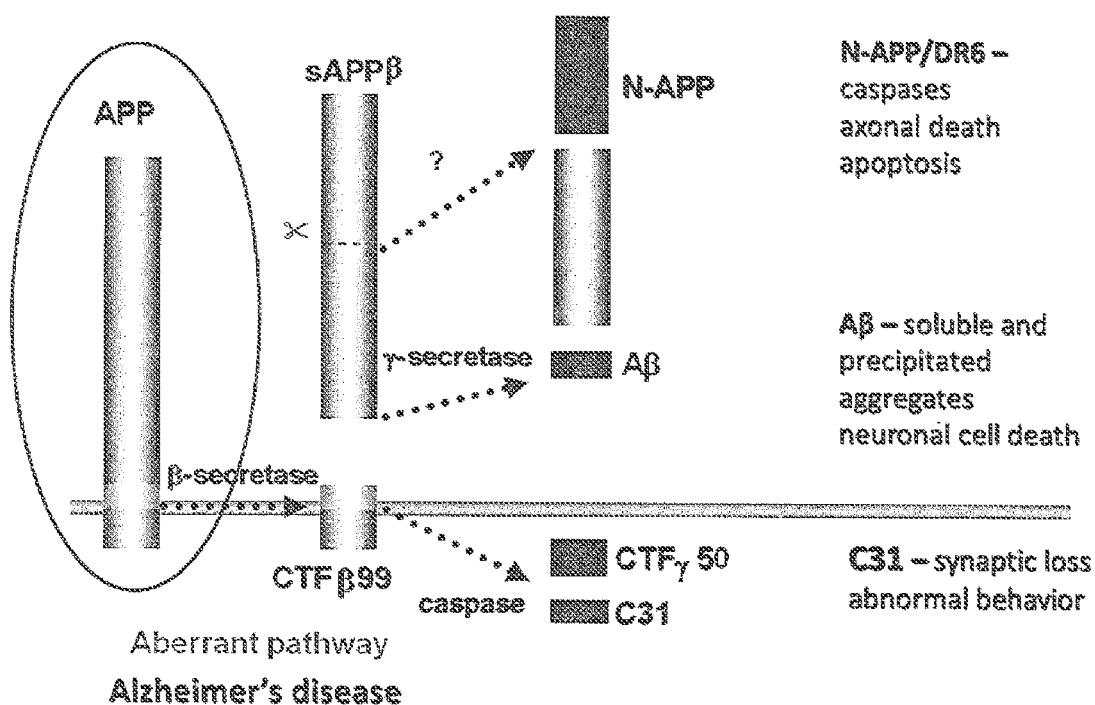
FIG. 2 is a scheme illustrating the downstream events relating to APP processing (adapted from Nicolaev et al., 2009, Nature 457:981-90, and Galvan et al., 2006, PNAS 103(18):7130-35).
Figure 3:
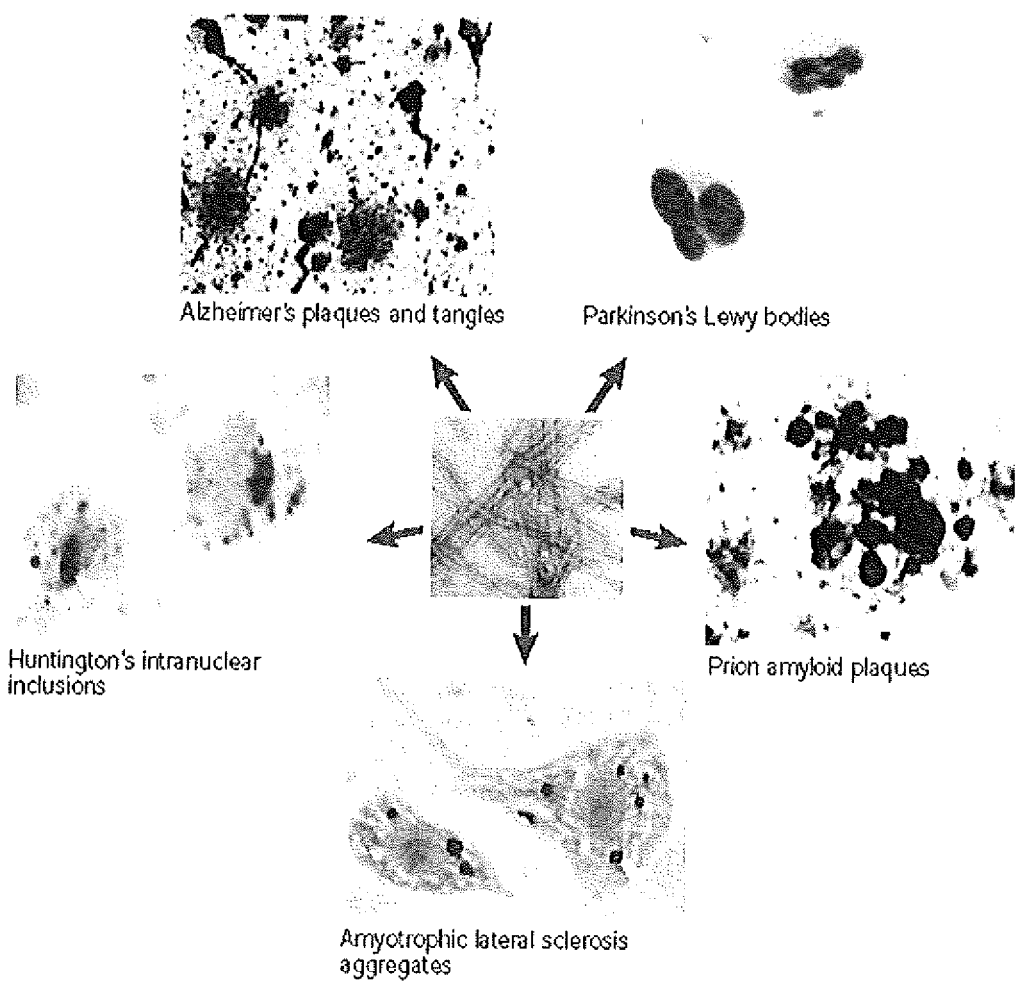
FIG. 3 is a series of photographs illustrating the role of cerebral aggregates in neurodegenerative diseases (AD: plaques and tangles; PD: Lewy bodies; HT: Huntington inclusions; TSE: prion amyloid plaque; ALS: superoxide dismutase inclusions)
Figure 4:
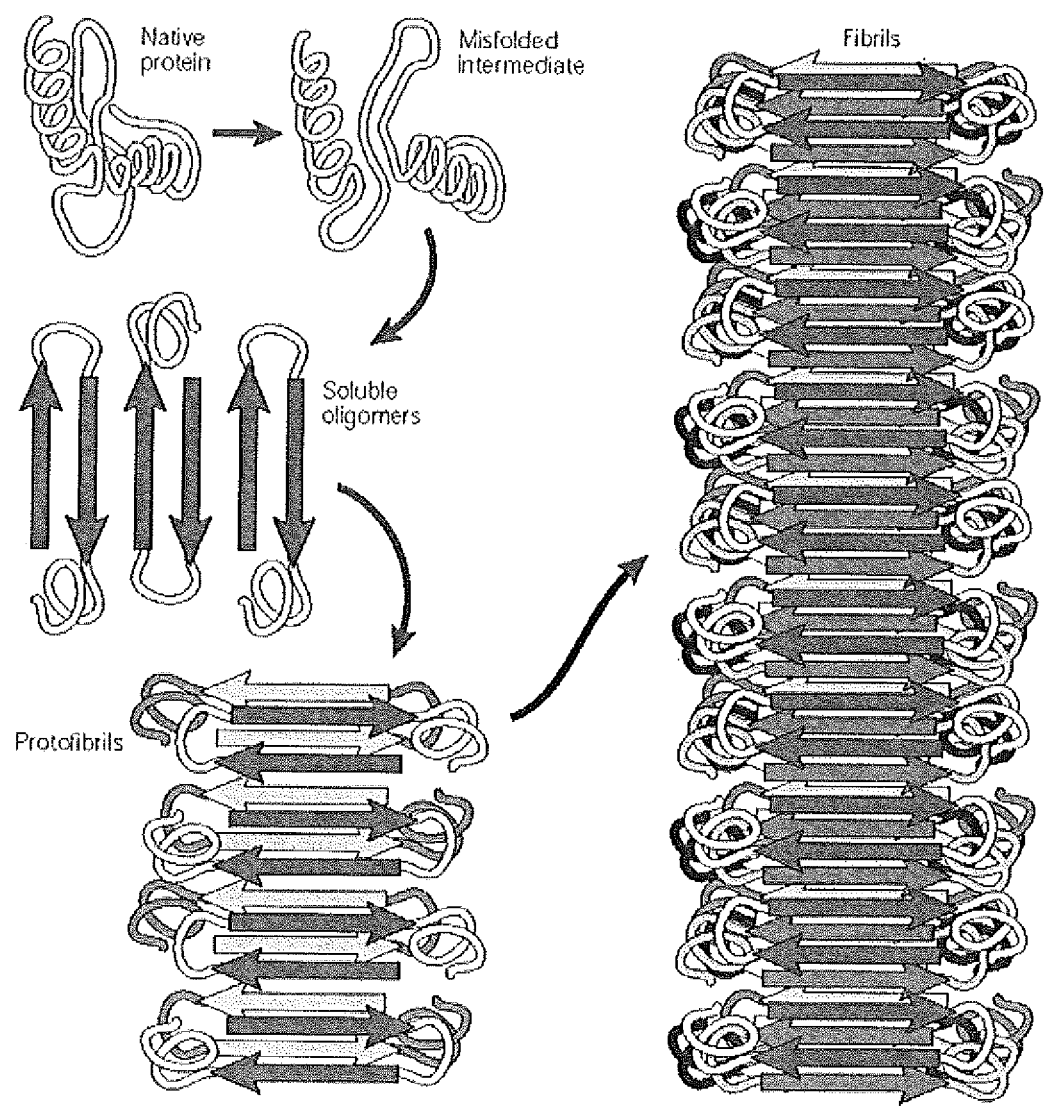
FIG. 4 is a scheme illustrating protein misfolding and aggregation.
Figure 5A:
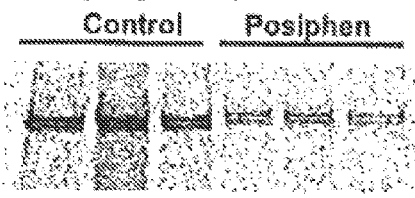
FIGS. 5A-5D, illustrates the finding that Compound (1) reduces newly synthesized APP without altering APP mRNA or total protein synthesis.
Figure 5B:
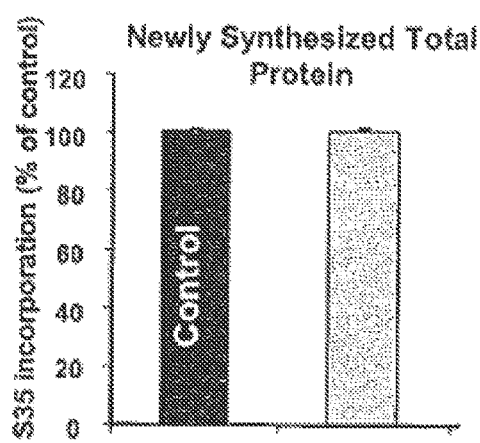
Figure 5C:
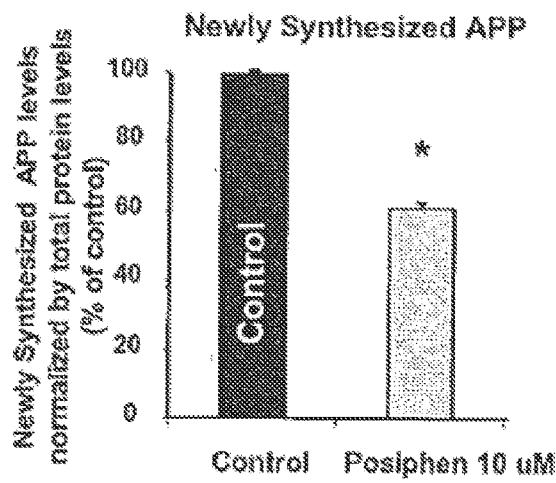
Figure 5D:
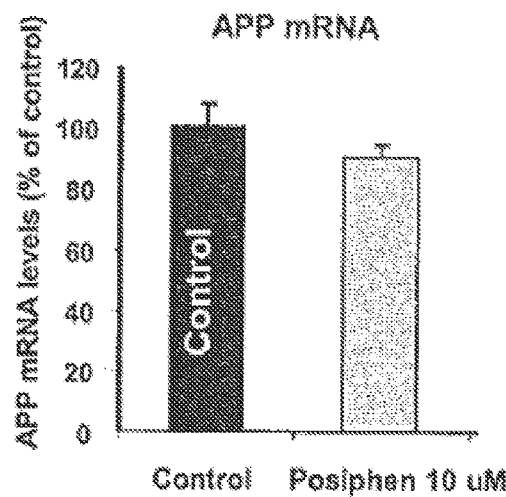
Figure 6A:
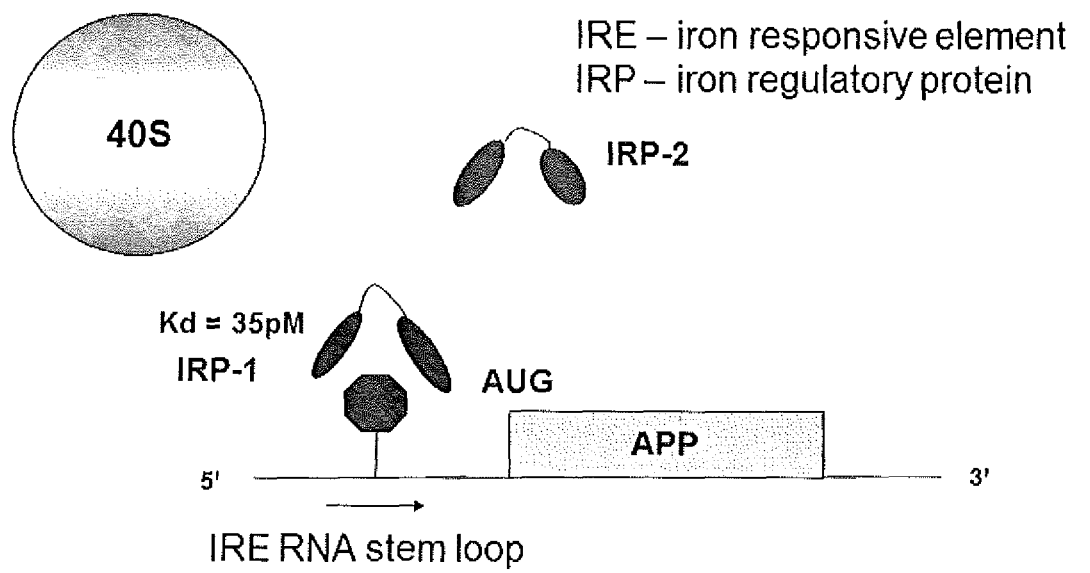
FIGS. 6A-6B, illustrate 5'-UTR of APP mRNA.
Figure 6B:
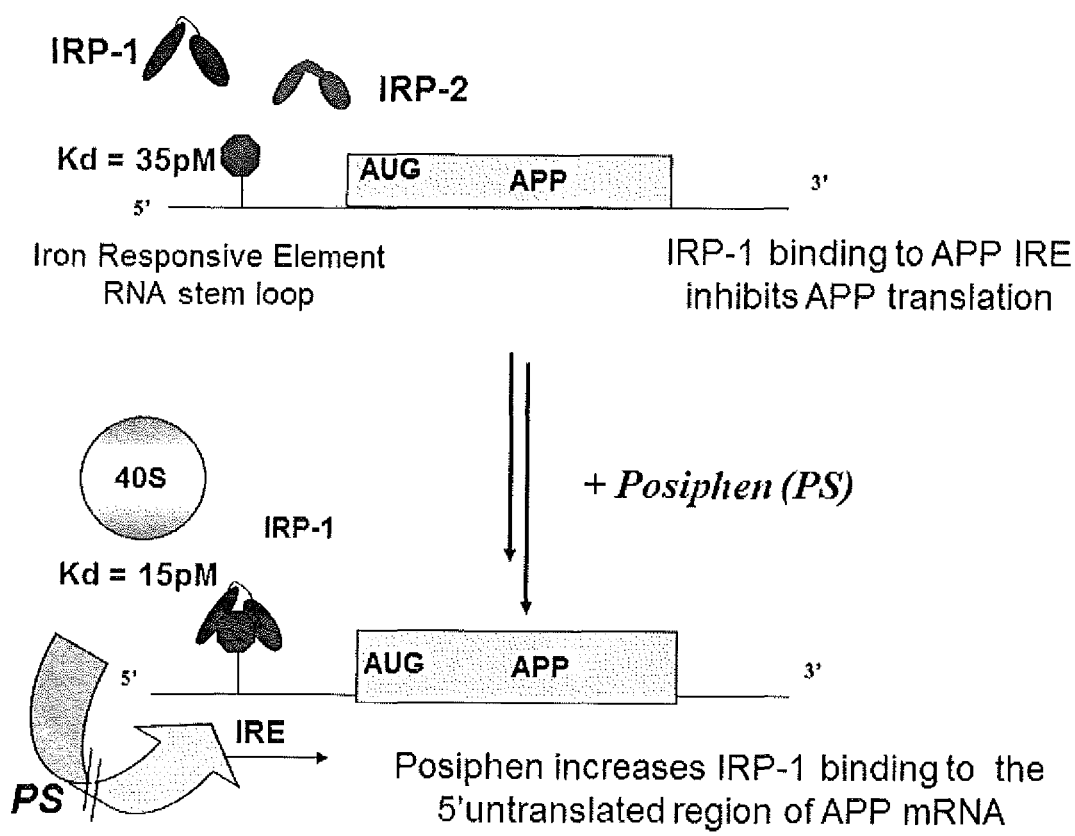
Figure 7A:
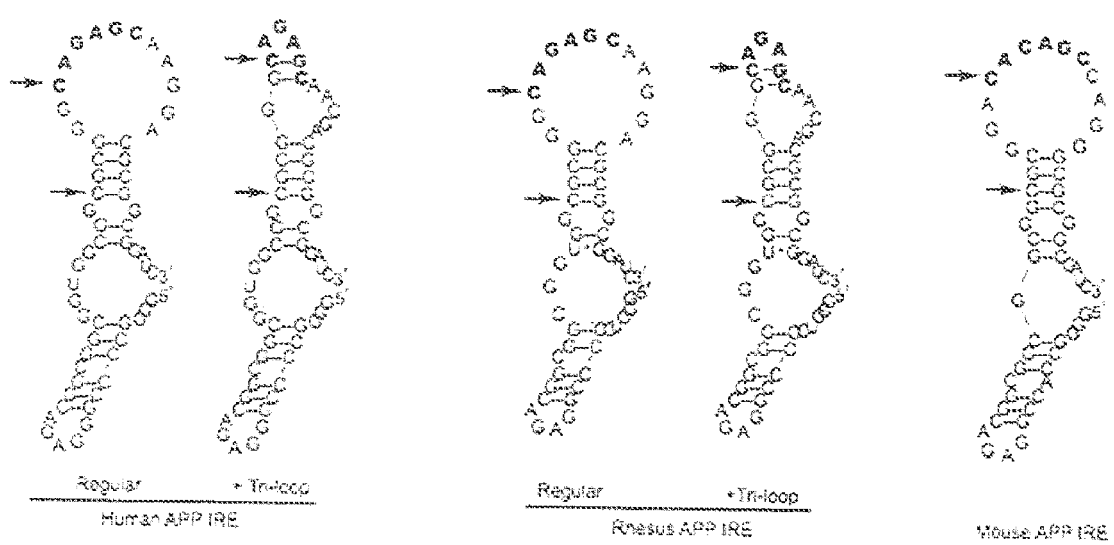
Figure 9A:
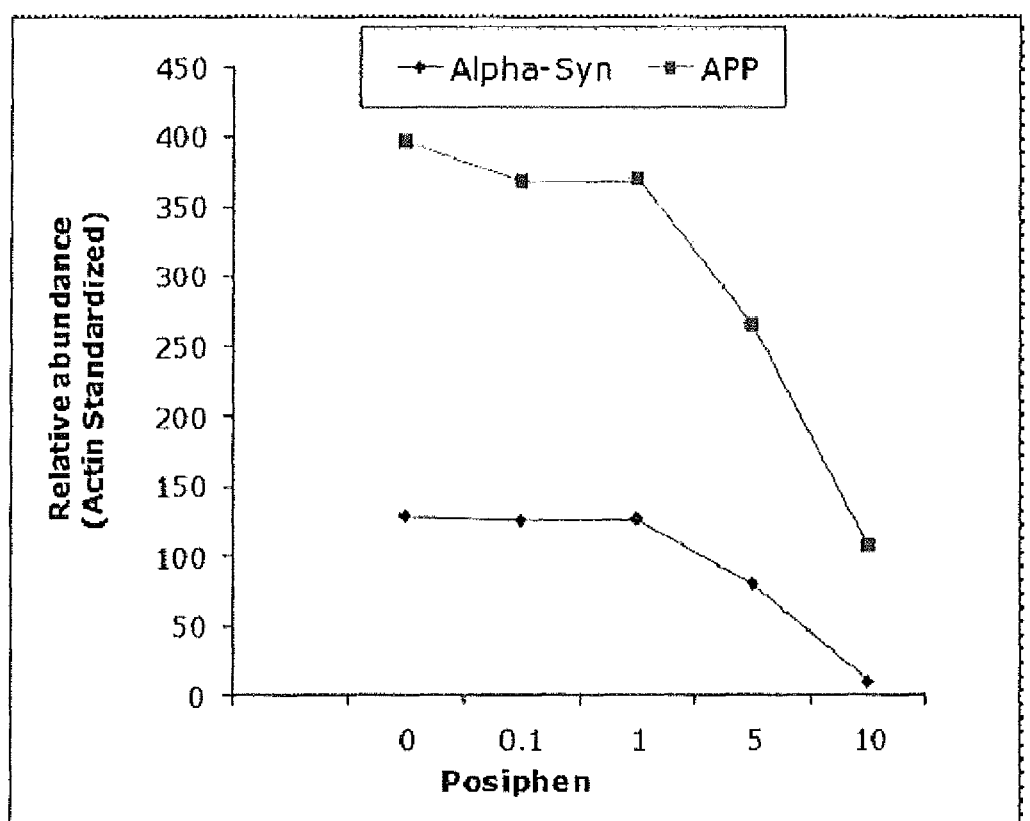
Figure 10:
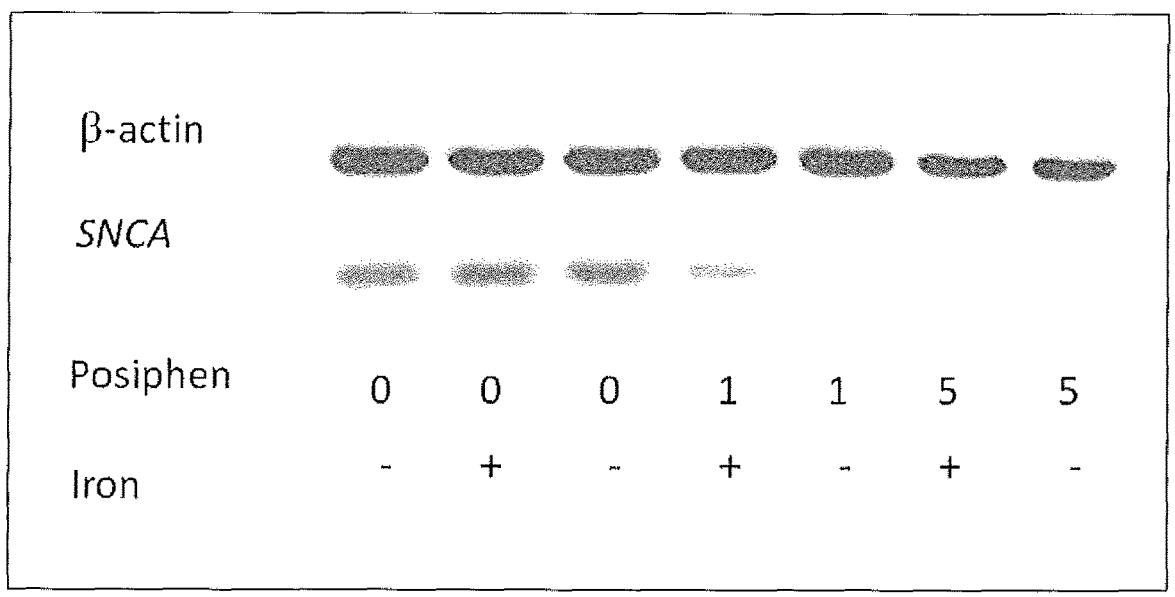
FIG. 10 is a representation of a gel illustrating that the inhibition of neural alpha-synuclein expression by Compound (1) is potentiated by cellular iron. Compound (1) decreased alpha-Syn levels dose-dependently in dopaminergic SH-SY5Y cells, as was reported for APP: The 5'UTRs of both APP & SNCA share 50% homology with the IRE H-ferritin mRNA (Friedlich et al., 2007). Quantitative Western blotting established the efficacy of Posiphen on alpha-Syn expression ($IC_{50}$<5 μM); after standardization for β-actin (Rogers et al. 2010).
Figure 11:
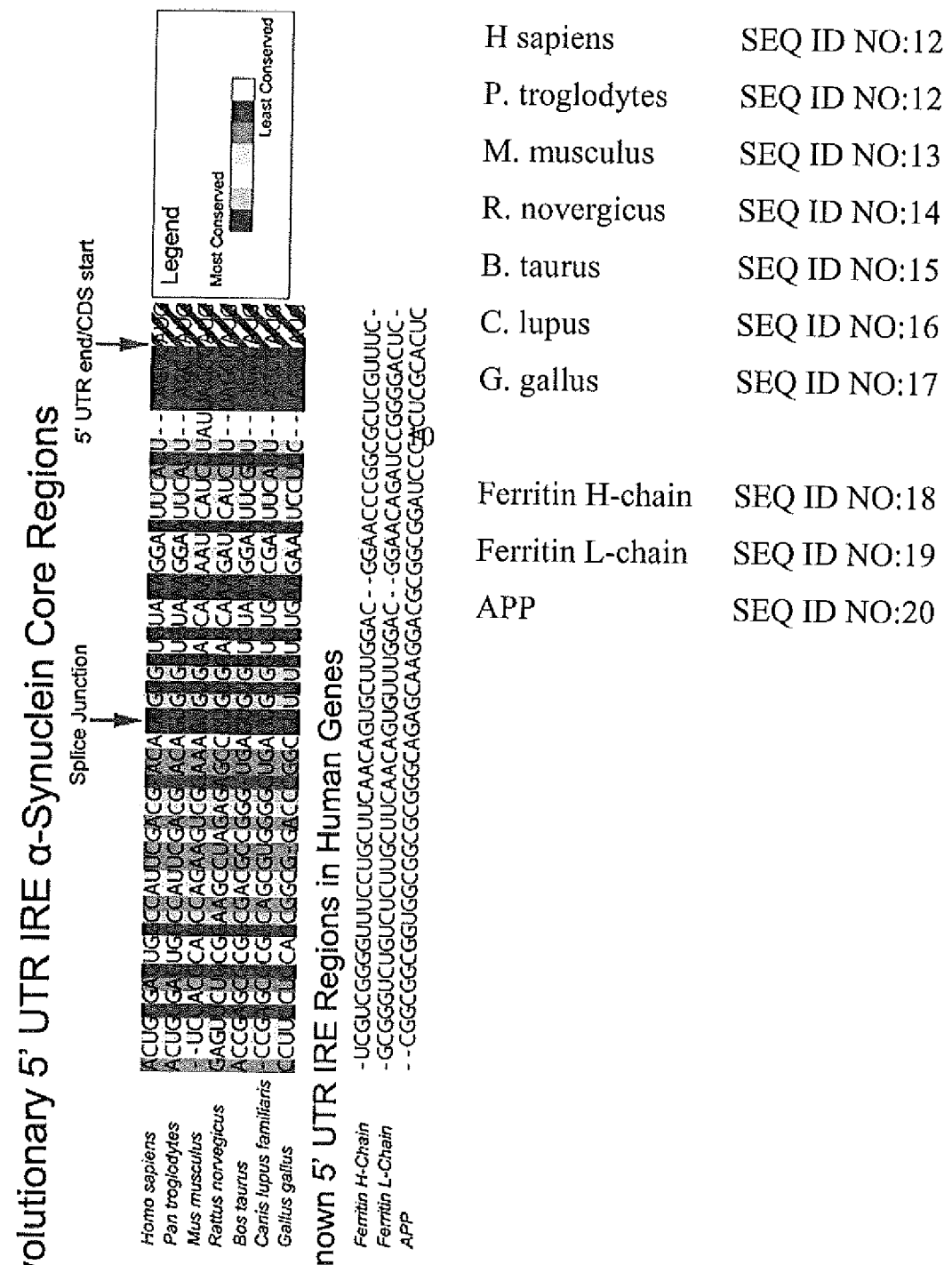
FIG. 11 is a scheme illustrating the 5' UTR sequence homology of SNCA in mammals and birds. *H sapiens*, SEQ ID NO:12; *P. troglodytes*, SEQ ID NO:12; *M. musculus*, SEQ ID NO:13; *R. novergicus*, SEQ ID NO:14; *B. taurus*, SEQ ID NO:15; *C. lupus*, SEQ ID NO:16; *G. gallus*, SEQ ID NO:17; Ferritin H-chain, SEQ ID NO:18; Ferritin L-chain, SEQ ID NO:19; APP, SEQ ID NO:20.
Figure 13:
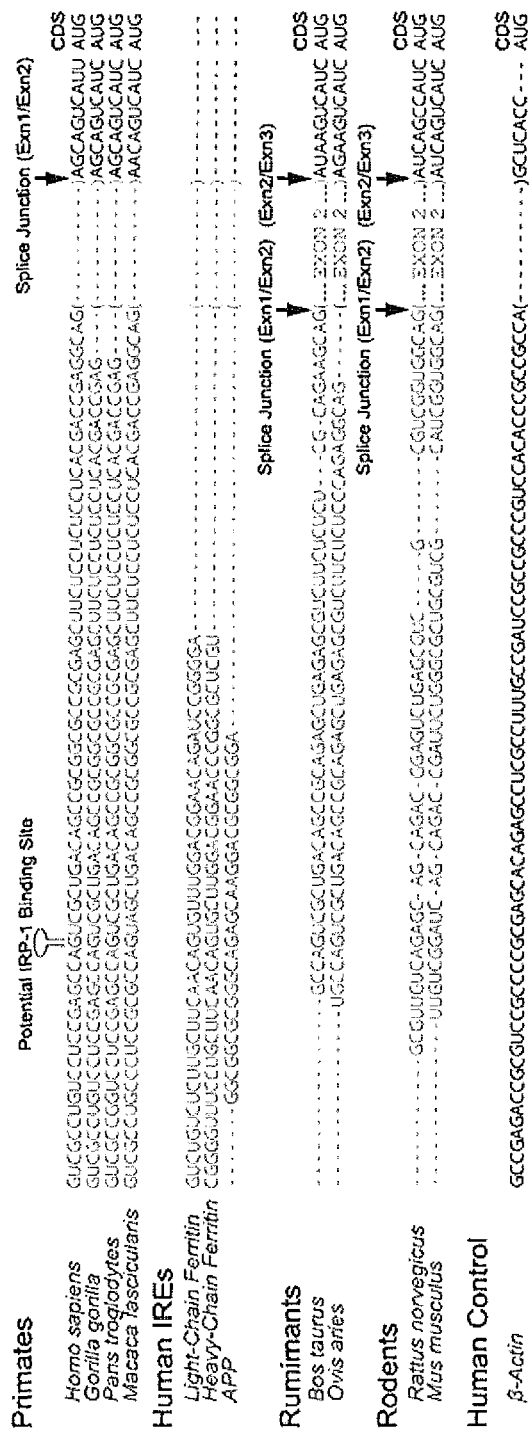
FIG. 13 is a scheme illustrating that the prion 5'UTR regions across species have putative IRP1 binding domains. *H. sapiens*, SEQ ID NO:21; *G. gorilla*, SEQ ID NO:22; *P. troglodytes*, SEQ ID NO:23; *M. fascicularis*, SEQ ID NO:24; light-chain ferritin, SEQ ID NO:25; heavy-chain ferritin, SEQ ID NO:26; APP, SEQ ID NO:27; *B. taurus*, SEQ ID NO:28; *O. aries*, SEQ ID NO:29; *R. norvegicus*, SEQ ID NO:30; *M. musculus*, SEQ ID NO:31; beta-actin, SEQ ID NO:32.
Figure 15:
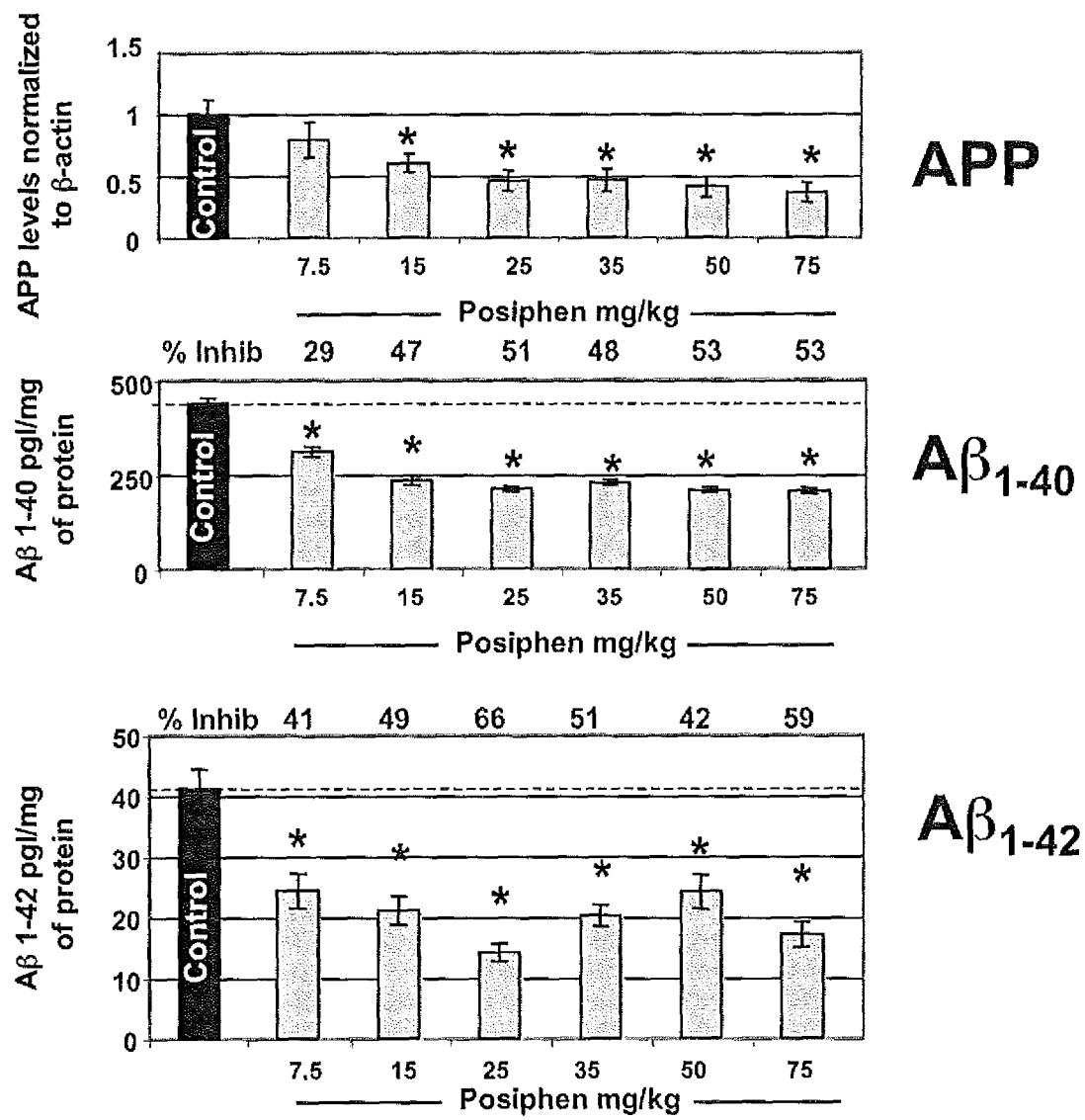
FIG. 15 is a series of graphs illustrating the in vivo reduction of APP, $Aβ_{40}$ and $Aβ_{42}$ levels in mouse brain by Compound (1). Drug was administered once daily ×21 day: APP—Western Blot, Aβ—Specific ELISA for 1-40 and 1-42 forms.
Figure 16:
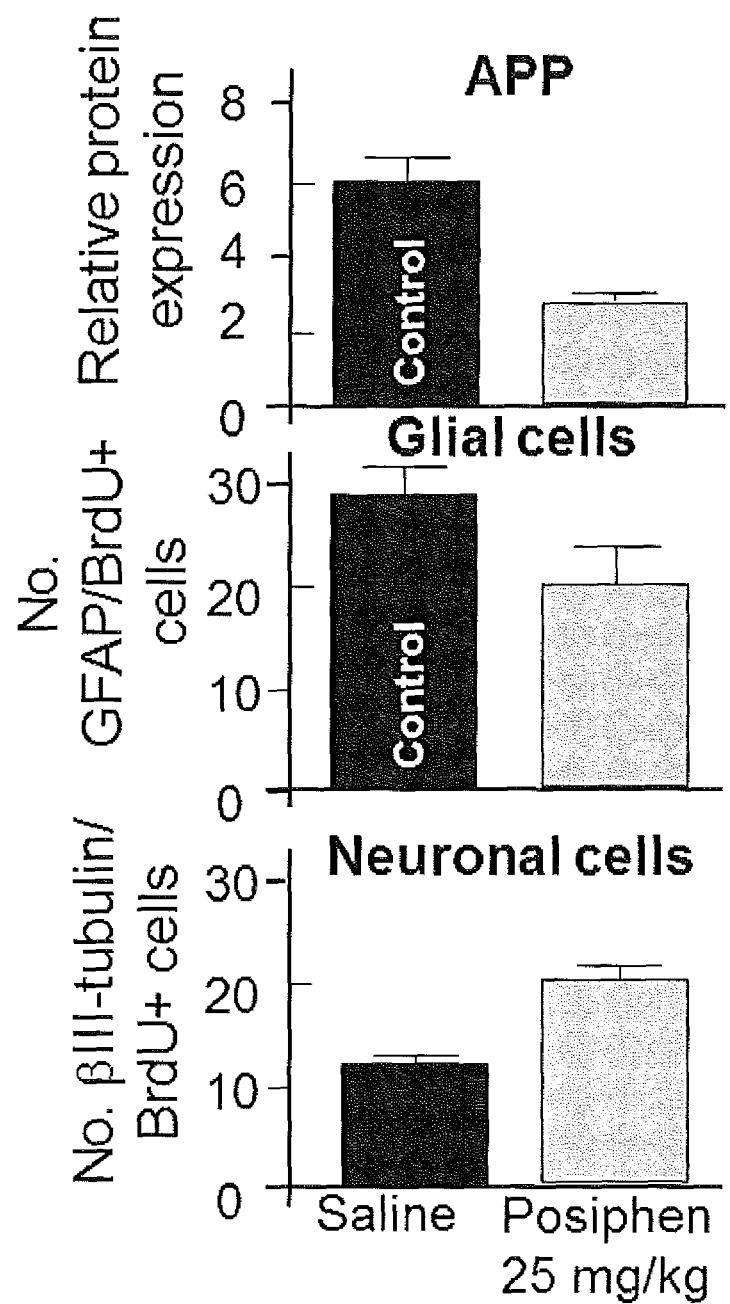
FIG. 16 is a series of graphs illustrating the effects of Compound (1) in Alzheimer APP23 transgenic mice. APP23 transgenic AD mice were treated with 25 mg of Compound (1) daily for 14 days. Compound (1) lowered APP levels in the brain of transgenic APP23 mice without lowering mRNA levels, improved stem cell survival in brain, increased stem cell migration to the hippocampus and cortex, and supported stem cell differentiation into neurons rather than into astrocytes and glia.
Figure 18:
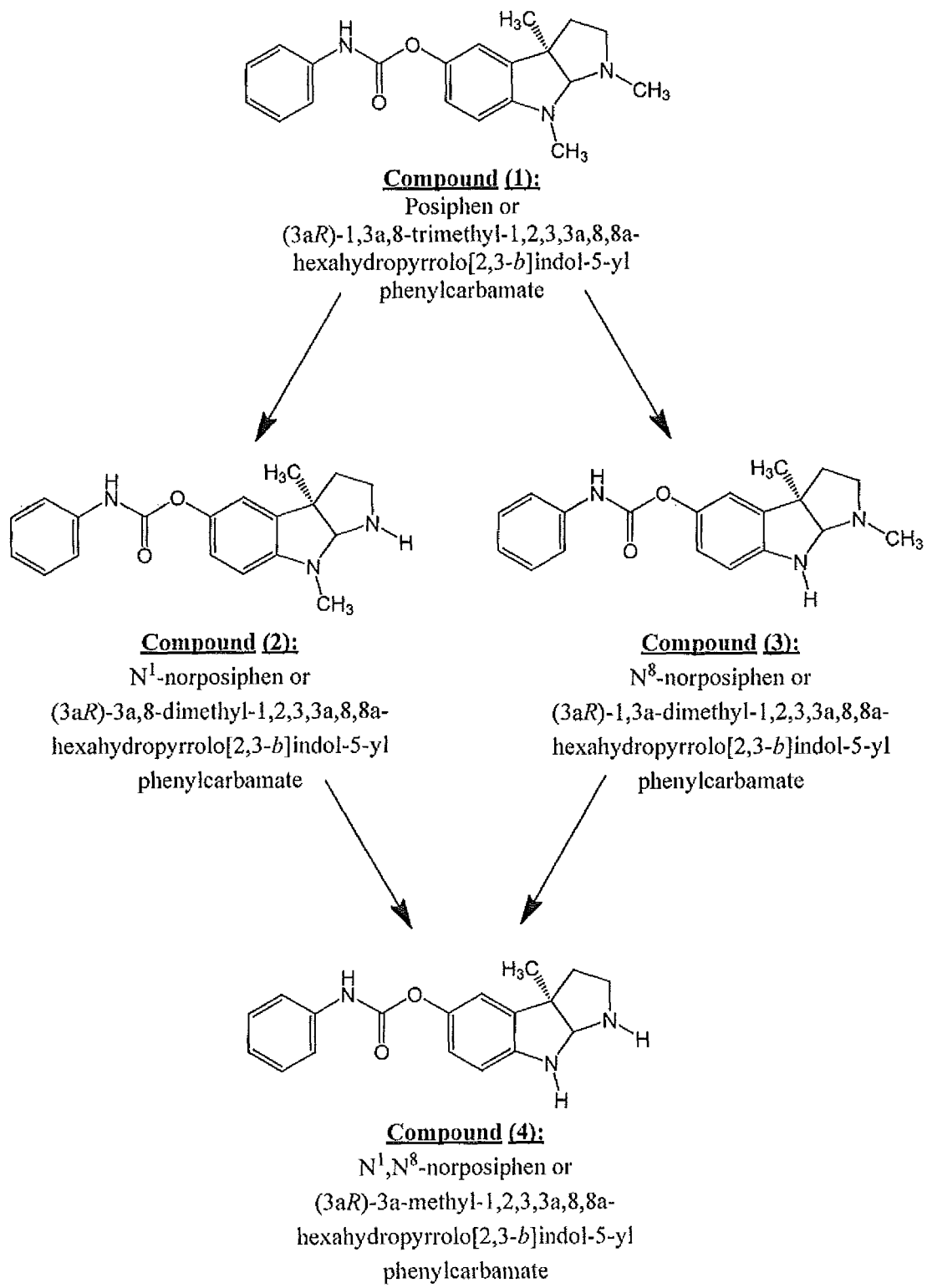
FIG. 18 illustrates selected metabolites of Posiphen® [Compound (1) or (3aR)-1,3a,8-trimethyl-1,2,3,3a,8,8a-hexahydropyrrolo[2,3-b]indol-5-yl phenylcarbamate]
Figure 20A:
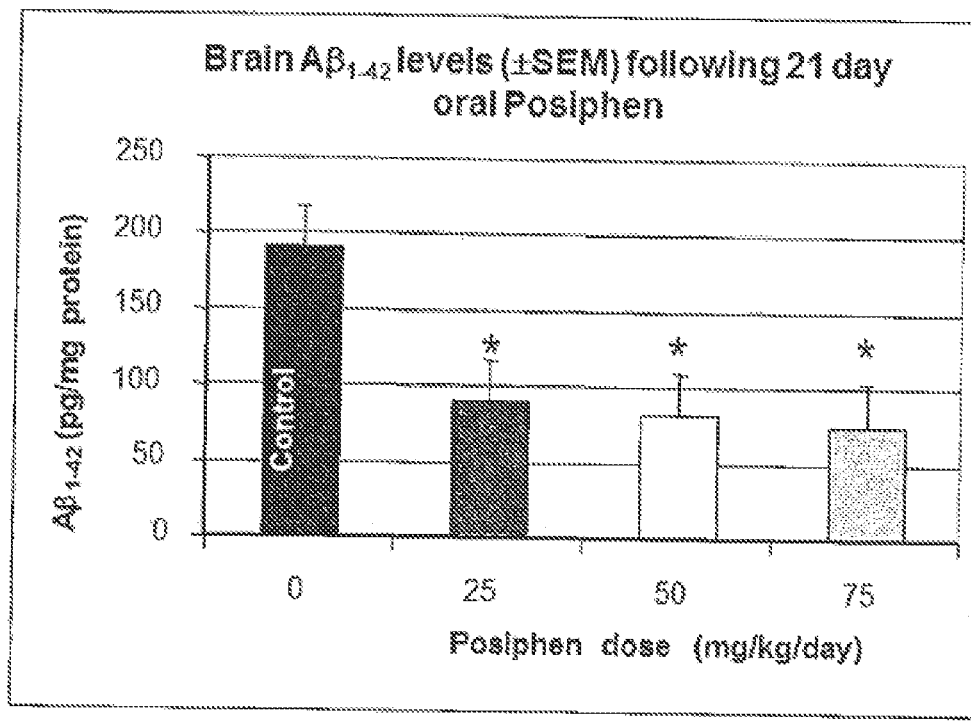
Figure 20B:
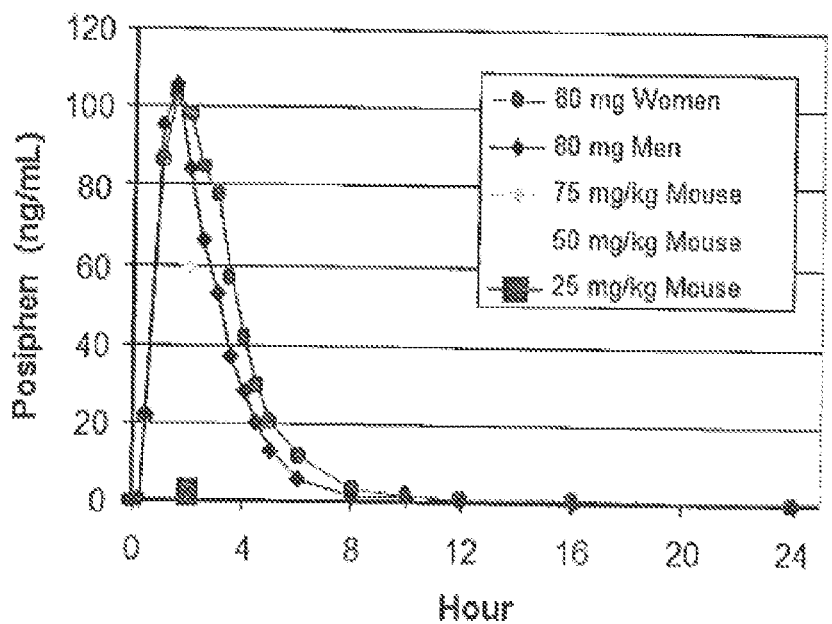

FIG. 20, comprising FIGS. 20A-20B, is a series of graphs illustrating inhibition of $Aβ_{42}$ levels by Compound (1), as a function of drug plasma levels. FIG. 20A illustrates brain $Aβ_{1-42}$ levels (±SEM) following 21 days of oral Compound (1), as a function of dose of Compound (1). FIG. 20B illustrates human and mouse plasma levels of Compound (1) after oral administration.

Figure 21A:
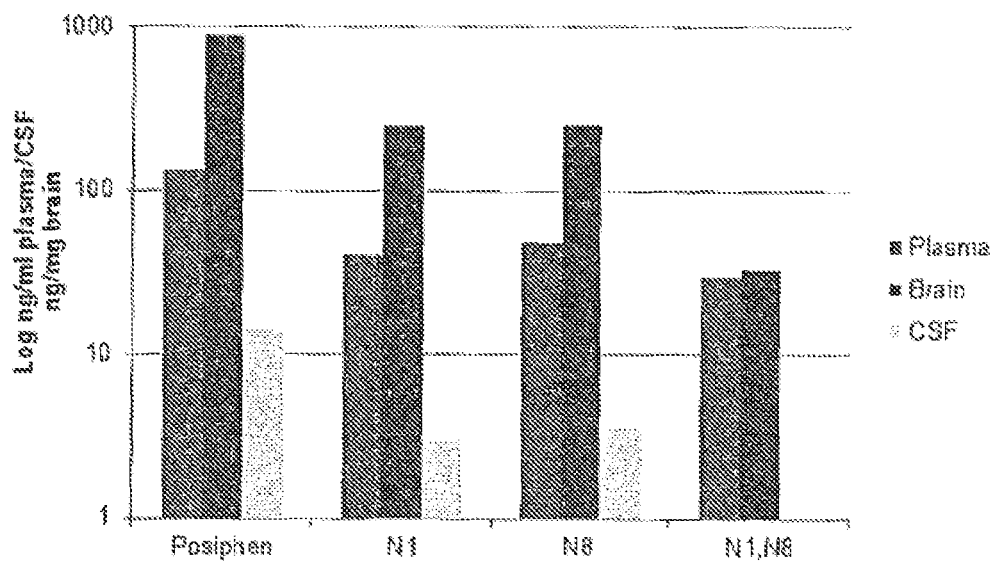
Figure 21B:
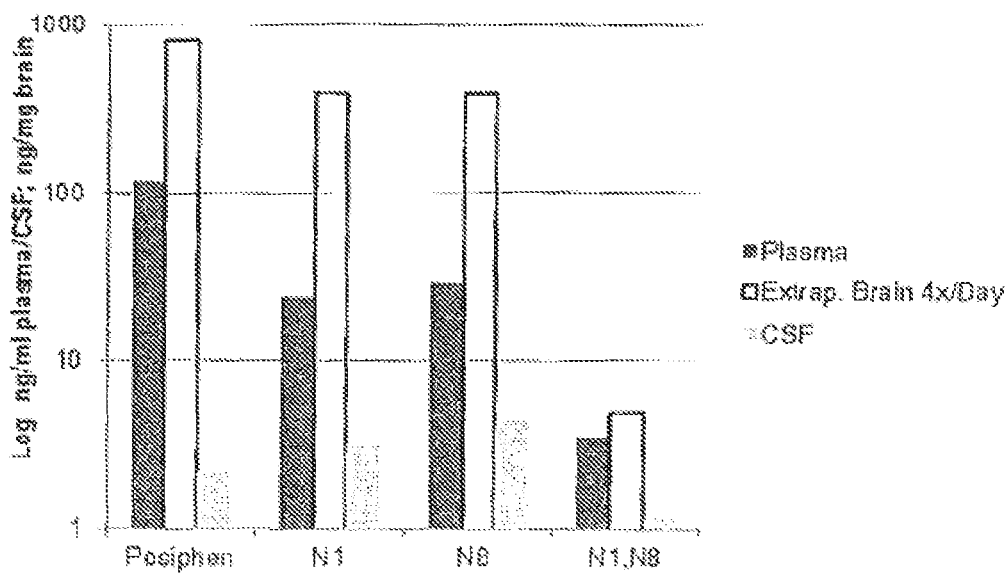

FIG. 21, comprising FIGS. 21A-21B, is a series of graphs illustrating the PK of Compound (1) and selected metabolites. FIG. 21A is a graph illustrating rat levels of Compound (1) and selected metabolites in plasma, brain and CSF (cerebrospinal fluid) at steady state. FIG. 21B is a graph illustrating human levels of Compound (1) and selected metabolites inn plasma, brain and CSF at steady state.

FIG. 22, comprising FIGS. 22A-22B, is a series of graphs illustrating the level of Compound (1) and selected metabolites in human plasma (FIG. 22A) and CSF (FIG. 22B) as a function of time after administration.

FIG. 23 is a table illustrating levels of biomarkers in CSF fluid for subjects after 10 days on Compound (1).

Figure 24:
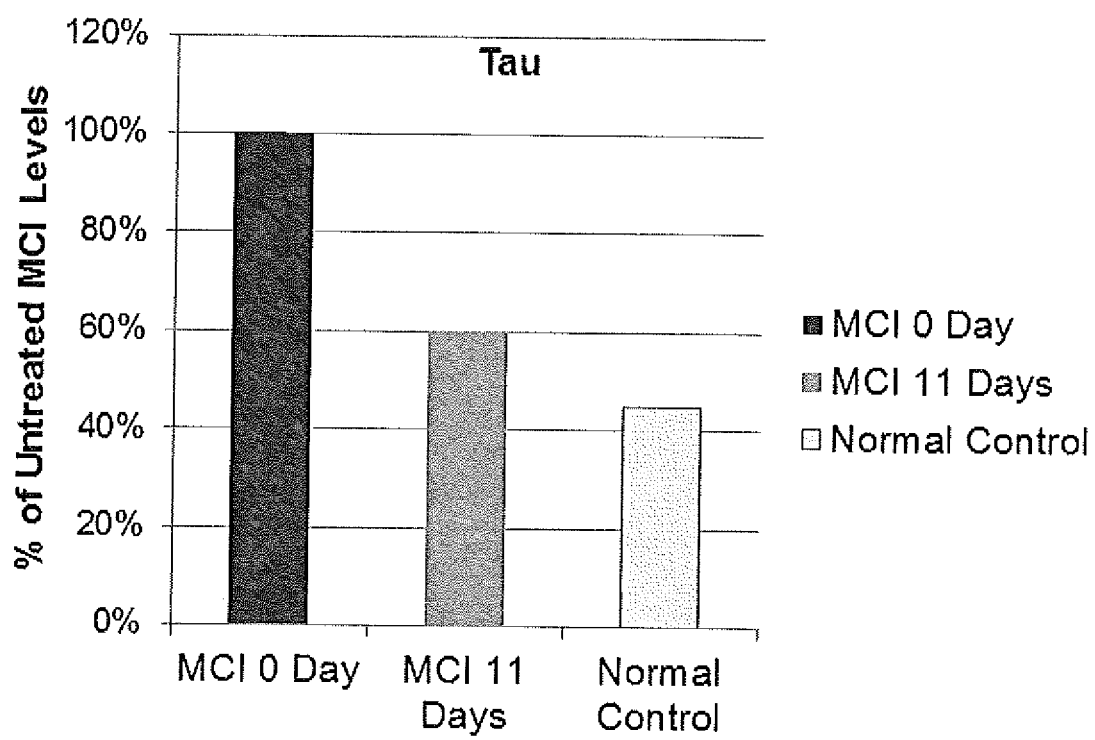

FIG. 24 is a graph illustrating the comparison of Tau before and after treatment with Compound (1) in healthy volunteers. Compound (1) was given for 10 days to mild cognitive impairment (MCI) patients, lowers their Tau levels back to the levels found in healthy volunteers.

Figure 25A:
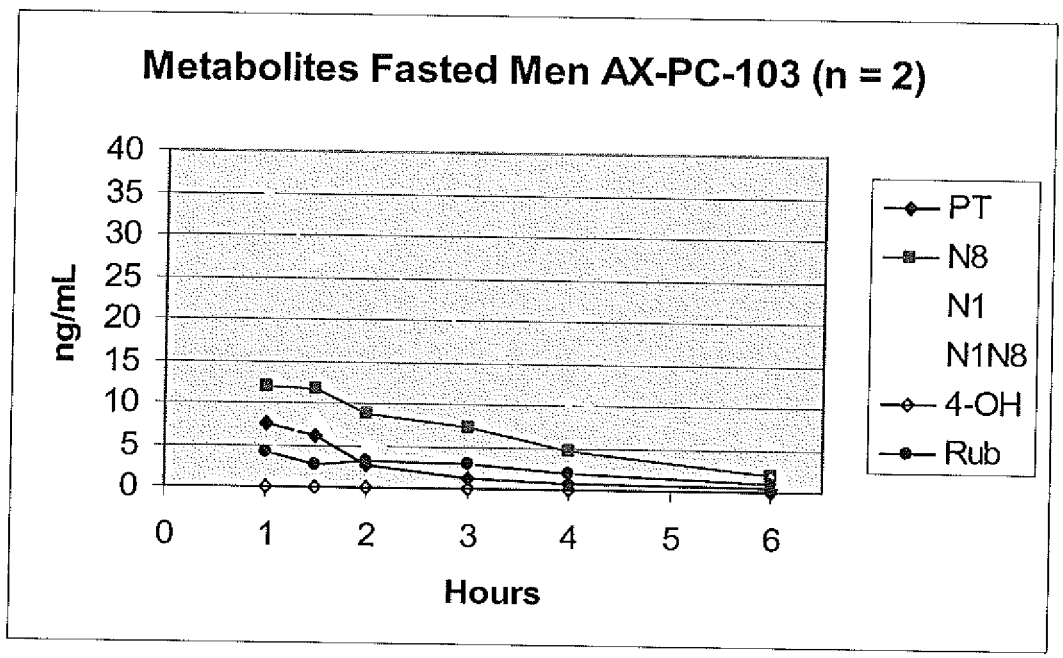
Figure 25B:
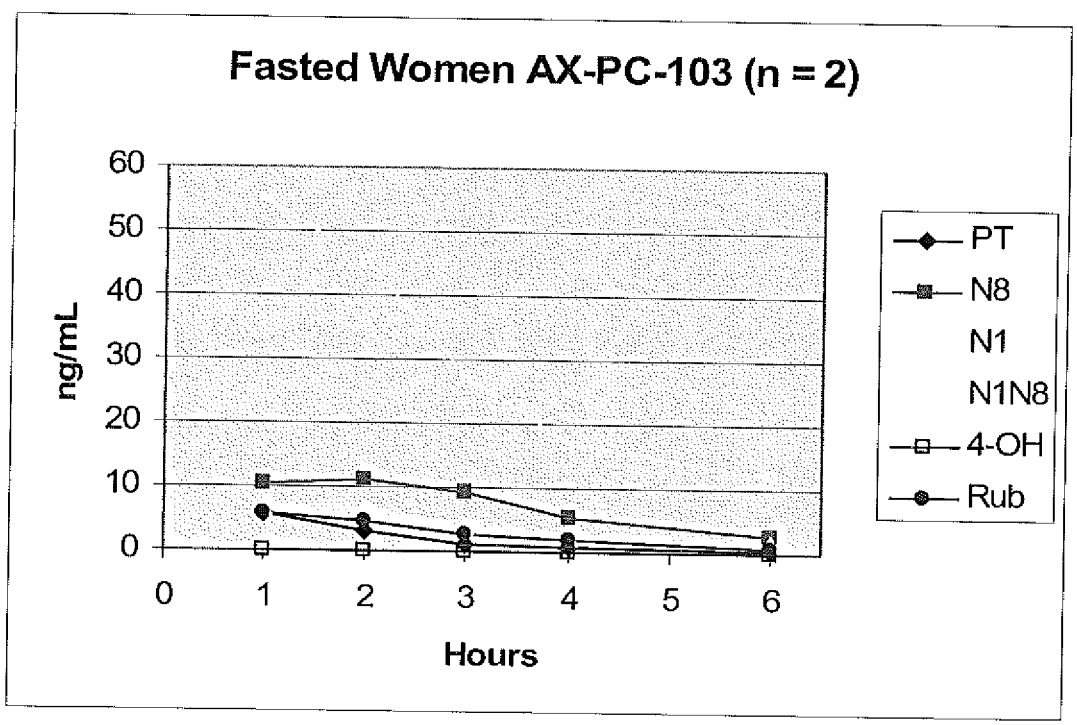

FIG. 25, comprising FIGS. 24A and 25B, illustrate the results of the determination of plasma metabolites of phenserine in men (FIG. 25A) and of phenserine in women (FIG. 25B), following 15 mg dose of phenserine on day 35 of study. PT: phenserine; $N^8$: $N^8$-desamine phenserine; $N^1$: $N^1$-desmethyl phenserine; $N^1,N^8$: $N^1,N^8$-desmethyl phenserine. Note that the metabolic profile of phenserine and Posiphen are totally different, with phenserine having a half life of less than one hour and the $N^1,N^8$-bisnorphenserine resulting in being the active compound. Posiphen has a half-life in plasma of 5 hours, with Posiphen being the active drug component and the $N^1,N^8$-bisnormetabolite being a minor and negligible contributor to the activity.

FIG. 26 is a series of tables summarizing PK parameters measured for Posiphen® and its metabolites in various species.

DETAILED DESCRIPTION OF THE INVENTION

The present invention includes an amount of Compound (1) or a salt thereof that, when administered to a subject, results in a minimum peak plasma circulating level and/or a minimum steady state plasma circulating level of Compound (1) or a selected metabolite thereof. Dosing of a subject with formulations comprising such amounts of the invention allow effective levels of the drug and/or any potentially active metabolite to be maintained in circulation in the subject for a specified period of time, leading to effective inhibition of AChE activity and/or effective reduction in levels of a neurotoxic aggregating protein in the subject. This circulating level is associated with inhibition of synthesis of a neurotoxic aggregating protein, such as but not limited to APP, Aβ, SNCA, NAC, SOD, HTT, Tau or a prion in the subject. In one aspect, the compositions and methods of the invention are thus useful for treating, ameliorating or preventing dementia in the subject. In one embodiment, the dementia is Alzheimer's disease, whereby administering the compositions of the invention inhibits synthesis of APP. In another embodiment the dementia is selected from the group consisting of Parkinson's disease, Huntington's disease, Prion's disease, Amyloid Lateral Sclerosis and a Tauopathy.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the terms "Posiphen®" and "Compound (1)" are used interchangeably to refer to (3aR)-1,3a,8-trimethyl-1,2,3,3a,8,8a-hexahydropyrrolo[2,3-b]indol-5-yl phenylcarbamate or a salt thereof.

As used herein, the terms "$N^1$-nor-Posiphen" and "Compound (2)" are used interchangeably to refer to (3aR)-3a,8-dimethyl-1,2,3,3a,8,8a-hexahydropyrrolo[2,3-b]indol-5-yl phenylcarbamate or a salt thereof.

As used herein, the terms "$N^8$-nor-Posiphen" and "Compound (3)" are used interchangeably to refer to (3aR)-1,3a-dimethyl-1,2,3,3a,8,8a-hexahydropyrrolo[2,3-b]indol-5-yl phenylcarbamate or a salt thereof.

As used herein, the terms "$N^1,N^8$-nor-Posiphen" and "Compound (4)" are used interchangeably to refer to (3aR)-3a-methyl-1,2,3,3a,8,8a-hexahydropyrrolo[2,3-b]indol-5-yl phenylcarbamate or a salt thereof.

As used herein, the term "APP" refers to amyloid precursor protein.

As used herein, the term "Aβ" refers to amyloid-β peptide.

As used herein, the term "SOD" refers to superoxide dismutase proteins and members of its family, such as SOD1 and SOD2. The term "SOD" includes any known mutations in superoxide dismutase proteins, such as A4V and G93A mutants in SOD1.

As used herein, the term "SNCA" refers to alpha-synuclein or non-A4 component of amyloid precursor.

As use herein, the term "NAC" refers to the alpha-synuclein fragment known as the non-Aβ component (NAC) of Alzheimer's disease amyloid.

As used herein, the term "prion" refers to an infectious agent composed of protein in a misfolded form.

As used herein, the term "TSE" refers to any form or variety of a transmissible spongiform encephalopathy.

As used herein, the term "TSE prion" refers to a prion associate with a TSE. Non-limiting examples of TSE prions are scrapie prion; transmissible mink encephalopathy (TME) prion; chronic wasting disease (CWD) prion; bovine spongiform encephalopathy (BSE) prion; feline spongiform encephalopathy (FSE) prion; exotic ungulate encephalopathy (EUE) prion; kuru prion; Creutzfeldt-Jakob disease (CJD) or Variant Creutzfeldt-Jakob disease (vCJD, nvCJD) prion; Gerstmann-Sträussler-Scheinker syndrome (GSS) prion; and fatal familial insomnia (FFI) prion.

As used herein, the term "HTT" refers to huntingtin or the Huntington protein.

As used herein, the term "Tau" refers to any of the products of alternative splicing from the gene designated MAPT.

As used herein, the term "neurotoxin aggregating protein" refers to a protein or family of proteins that has neurotoxic effect upon accumulating in a tissue of the brain, such as the brain tissue. Non-limiting examples of neurotoxin aggregating proteins are APP, Aβ, SOD, SNCA, NAC, TSE amyloid plaque, HTT, and Tau.

As used herein, the terms "protein", "peptide" and "polypeptide" are used interchangeably, and refer to a compound comprised of amino acid residues covalently linked by peptide bonds.

By the term "specifically binds," as used herein, is meant a molecule, such as an antibody or a small molecule, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

"Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

As used herein, the "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric; citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glutamine) and procaine. All of these salts may be prepared by convention& means from the corresponding free base compound by reacting, for example, the appropriate acid or base with the corresponding free base.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis "Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions of the Invention

In one aspect, the compound useful within the methods of the invention is Compound (1):

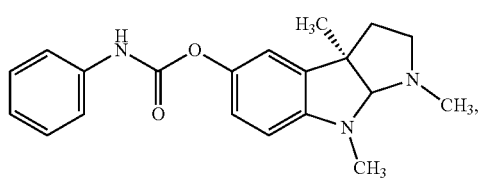

(1)

or a salt thereof.

Compound (1) or any other compound useful within the methods of the invention may be synthesized using techniques well-known in the art of organic synthesis or obtained from commercial sources. In a non-limiting example, Compound (1) may be synthesized according to the disclosure in U.S. Pat. No. 6,495,700, incorporated herein in its entirety.

The invention includes an amount of Compound (1) or a salt thereof, wherein administering the amount to a subject results in a peak plasma circulating level of Compound (1) ranging from about 10 ng/ml to about 160 ng/mL in the subject.

In one embodiment, the peak plasma circulating level ranges from about 80 ng/mL to about 160 ng/ml in the subject. In another embodiment, the peak plasma circulating level is reached within about 6 hours after the administering. In yet another embodiment, the peak plasma circulating level is reached within about 3 hours after the administering. In yet another embodiment, the plasma circulating level of Compound (1) is equal to or greater than about 20 ng/mL for at least 12 hours after the administering. In yet another embodiment, the plasma circulating level of Compound (1) is equal to or greater than about 20 ng/mL for at least 9 hours after the administering. In yet another embodiment, the administering results in a peak plasma concentration of Compound (2) ranging from about 15% to about 30% of the peak plasma concentration of Compound (1) in the subject. In yet another embodiment, the administering results in a peak plasma concentration of Compound (3) ranging from about 15% to about 30% of the peak plasma concentration of Compound (1) in the subject. In yet another embodiment, the administering results in a peak plasma concentration of Compound (4) ranging from about 1% to about 9% of the peak plasma concentration of Compound (1) in the subject. In yet another embodiment, the administering results in a steady state plasma concentration of Compound (1) of at least about 100 ng/ml in the subject. In yet another embodiment, the administering results in a steady state plasma concentration of Compound (2) of at least about 10 ng/ml in the subject. In yet another embodiment, the administering results in a steady state plasma concentration of Compound (3) of at least about 10 ng/ml in the subject. In yet another embodiment, the administering results in a steady state plasma concentration of Compound (4) of at least about 3 ng/ml in the subject. In yet another embodiment, the administering results in a brain level of Compound (1) that ranges from about 4 to about 10 times the plasma level of Compound (1) in the subject. In yet another embodiment, the brain level of Compound (2) ranges from about 15% to about 150% of the brain level of Compound (1) in the subject. In yet another embodiment, the brain level of Compound (3) ranges from about 15% to about 150% of the brain level of Compound (1) in the subject. In yet another embodiment, the brain level of Compound (4) is lower than the brain level of Compound (2) or Compound (3) in the subject. In yet another embodiment, the subject is a human. In yet another embodiment, the peak plasma circulating level of Compound (1) is lower than the peak toxic level of Compound (1) in the plasma of the subject. In a non-limiting embodiment, the toxic level of Compound (1) in the plasma is greater than 80 ng/mL.

Salts of the Compounds of the Invention

The compounds described herein may form salts with acids or bases, and such salts are included in the present invention. In one embodiment, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base Methods of the Invention The invention includes a method of inhibiting production of a neurotoxic aggregating protein, such as APP, Aβ, SNCA, NAC, SOD, Tau, TSE prion and HTT in a subject. The method comprises administering to the subject a pharmaceutical composition comprising a pharmaceutically acceptable carrier and an amount of Compound (1) or a salt thereof, wherein administering the composition to the subject results in a peak plasma circulating level of Compound (1) ranging from about 10 ng/ml to about 160 ng/ml in the subject, whereby the production of the neurotoxic aggregating protein in the subject is inhibited.

The invention includes a method of treating dementia in a subject. The method comprising administering to the subject a pharmaceutical composition comprising a pharmaceutically acceptable carrier and an amount of Compound (1) or a salt thereof, wherein administering the composition to the subject results in a peak plasma circulating level of Compound (1) ranging from about 10 ng/ml to about 160 ng/ml in the subject, whereby the dementia in the subject is treated.

In one embodiment, the peak plasma circulating level ranges from about 80 ng/mL to about 160 ng/ml in the subject. In another embodiment, the peak plasma circulating level is reached within about 6 hours after the administering. In yet another embodiment, the peak plasma circulating level is reached within about 3 hours after the administering. In yet another embodiment, the plasma circulating level of Compound (1) is equal to or greater than about 20 ng/mL for at least 12 hours after the administering. In yet another embodiment, the plasma circulating level of Compound (1) is equal to or greater than about 20 ng/mL for at least 9 hours after the administering. In yet another embodiment, the administering results in a peak plasma concentration of Compound (2) ranging from about 15% to about 30% of the peak plasma concentration of Compound (1) in the subject. In yet another embodiment, the administering results in a peak plasma concentration of Compound (3) ranging from about 15% to about 30% of the peak plasma concentration of Compound (1) in the subject. In yet another embodiment, the administering results in a peak plasma concentration of Compound (4) ranging from about 1% to about 9% of the peak plasma concentration of Compound (1) in the subject. In yet another embodiment, the administering results in a steady state plasma concentration of Compound (1) of at least about 100 ng/ml in the subject. In yet another embodiment, the administering results in a steady state plasma concentration of Compound (2) of at least about 10 ng/ml in the subject. In yet another embodiment, the administering results in a steady state plasma concentration of Compound (3) of at least about 10 ng/ml in the subject. In yet another embodiment, the administering results in a steady state plasma concentration of Compound (4) of at least about 3 ng/ml in the subject. In yet another embodiment, the administering results in a brain level of Compound (1) that ranges from about 4 to about 10 times the plasma level of Compound (1) in the subject. In yet another embodiment, the brain level of Compound (2) ranges from about 15% to about 150% of the brain level of Compound (1) in the subject. In yet another embodiment, the brain level of Compound (3) ranges from about 15% to about 150% of the brain level of Compound (1) in the subject. In yet another embodiment, the brain level of Compound (4) is lower than the brain level of Compound (2) or Compound (3) in the subject. In yet another embodiment, the subject is a human. In yet another embodiment, the peak plasma circulating level of Compound (1) is lower than the peak toxic level of Compound (1) in the plasma of the subject. In a non-limiting embodiment, the toxic level of Compound (1) in the plasma is greater than 80 ng/mL.

In one embodiment, the administering results in a reduction of or greater than about 25% in a cerebrospinal fluid marker selected from the group consisting of sAPPα, sAPPβ, Tau and pTau in the subject. In another embodiment, the administering results in a reduction of or greater than about 30% in a cerebrospinal fluid marker selected from the group consisting of sAPPα, sAPPβ, Tau and pTau in the subject. In yet another embodiment, the subject is a human. In yet another embodiment, the dementia is Alzheimer's disease. In yet another embodiment, the dementia is selected from the group consisting of Parkinson's disease, Huntington's disease, Prion's disease, Amyloid Lateral Sclerosis and a tauopathy.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 µg to about 10 mg per kilogram of body weight of the animal. More preferably, the dosage will vary from about 3 µg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 1,000 mg, about 2 mg to about 950 mg, about 4 mg to about 900 mg, about 7.5 mg to about 850 mg, about 15 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid, Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way of a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (eg., olive oil/PEG7), biovera oil, wax (eg., jojoba wax), squalene, myristate (eg., isopropyl myristate), triglycerides (eg., caprylic triglyceride), Solulan 98, cocoa butter, shea butter, alcohol (eg., behenyl alcohol), stearate (eg., glycerol-monostearate), chelating agents (eg., EDTA), propylene glycol, SEPIGEL (Seppic, Inc., Fairfield, N.J.), silicone and silicone derivatives (eg., dimethicone, cyclomethicone), vitamins (eg., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Kits of the Invention

The invention also includes a kit comprising a compound useful within the methods of the invention and an instructional material that describes, for instance, administering the compound to a subject as a prophylactic or therapeutic treatment or a non-treatment use as described elsewhere herein. In an embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

Example 1

Inhibition of $A\beta_{1-42}$ Levels

In order to correlate plasma and tissue levels of Compound (1) with reduction of amyloid protein levels, mice were administered Compound (1) orally at various doses (25 mg/kg/day; 50 mg/kg/day; and 100 mg/kg/day) for a period of 21 days. The $A\beta_{1-42}$ levels in the brain of the mice were determined (FIG. 20A), using a sandwich ELISA assay.

Mice and humans were orally dosed with Compound (1) and the plasma levels of this compound were determined as a function of time after administration (FIG. 20B). The plasma concentrations of Compound (1) were determined by LC/MS/MS. The data illustrated in FIGS. 20A and 20B suggest that the levels of Compound (1) in human plasma upon oral administration of this compound are greater than the levels of Compound (1) in mice for which a reduction in amyloid protein was observed.

Example 2

Proof of Mechanism Study

For a proof of mechanism study of Compound (1), patients suffering from mild cognitive impairment (MCI) were treated with Compound (1) for 10 days. The patients were dosed with 4×60 mg Compound (1) for 10 days orally, using Posiphen® powder filled into gelatin capsules. Cerebrospinal fluid (CSF) and plasma were drawn from the subjects over a 12 hour period on day 0 and day 11.

Pharmacokinetic analysis was performed for Compound (1) and selected metabolites: $N^1$-norposiphen, $N^8$-norposiphen, and $N^1,N^8$-norposiphen. Pharmacodynamic analysis was performed for APP protein and other AD associated biomarkers in CSF and plasma: APP, $A\beta_{1-40}$, $A\beta_{1-42}$, N-APP, AChEI, BChEI, Tau/p-Tau, NGF, BDNF, and inflammatory factors.

The following schedule of PK monitoring was implemented for each species:
(a) in the mouse, oral/gavage or ip/injection: plasma and brain were analyzed at 90, 120, and 180 minutes after administration of the drug, on days 1, 10, 14 and 21.
(b) in the rat, oral/gavage or ip/injection or infusion pump/se: plasma, brain and CSF were analyzed at 90 minutes after administration of drug, on days 1, 5 and 10 days of infusion.
(c) in the dog, oral/gelatin capsules filled with Posiphen powder: plasma was analyzed 0 to 36 hours after administration of the drug.
(d) in humans, plasma and CSF were analyzed 0 to 12 hours, after administration of the drug.

The binding of Compound (1) and metabolites to brain proteins was determined to be ~96% (rat and human brain homogenate).

FIG. 21A illustrates the levels of Compound (1) and selected metabolites in the rat plasma, brain and CSF samples under steady state conditions. FIG. 21B illustrates the levels of Compound (1) and selected metabolites in the human plasma, brain and CSF samples under steady state conditions.

The levels of Compound (1) and selected metabolites in human plasma (FIG. 22A) and human CSF (FIG. 22B) were determined. Interestingly, the half-life of Compound (1) in human plasma was determined to be about 5 hours, whereas the half-life of Compound (1) in human CFS was determined to be about 12 hours. This was corroborated by measuring half-life of Posiphen® in brains of mice.

Example 3

Effect of Administration of Posiphen® on Human Biomarkers

Levels of biomarkers were monitored in humans after 10 days of administration of Compound (1). The results are summarized in FIG. 23.

Example 4

Proposed Phase II Study

In the proposed Phase II study, very early stage (prodome) AD patients are treated for 1 year. The study comprises 4 to 5 arms, each one with about 100 people. The arms comprise (i) Compound (1) plus Aricept and Aricept control, or (ii) Compound (1) and Aricept plus placebo controls. CSF biomarkers are monitored, and imaging studies and cognitive tests are performed. Safety of subjects is monitored, and if study meets at least any two endpoints, it is then progressed to Phase III.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

```
                        SEQUENCE LISTING

<160> NUMBER OF SEQ ID NOS: 32

<210> SEQ ID NO 1
<211> LENGTH: 57
<212> TYPE: DNA
<213> ORGANISM: Homo sapiens

<400> SEQUENCE: 1
ggggccccgg gagacggcgg cggtggcggc gcgggcagag caaggacgcg gcggatc        57

<210> SEQ ID NO 2
<211> LENGTH: 54
<212> TYPE: DNA
<213> ORGANISM: Mus musculus

<400> SEQUENCE: 2
ggggccaccg gagacggcgg cggcggcgcg gacacagcca gggcgcggcg gatc           54

<210> SEQ ID NO 3
<211> LENGTH: 54
<212> TYPE: DNA
<213> ORGANISM: Macaca Mulatta

<400> SEQUENCE: 3 gggtccccccg gagacggcgg cggtggcgcg ggcagagcaa ggacgcggcg gatc          54

<210> SEQ ID NO 4
<211> LENGTH: 57
<212> TYPE: DNA
<213> ORGANISM: Homo sapiens

<400> SEQUENCE: 4
gttcggcggt cccgcgggtc tgtctcttgc ttcaacagtg tttggacgga acagatc        57

<210> SEQ ID NO 5
<211> LENGTH: 57
<212> TYPE: DNA
<213> ORGANISM: Homo sapiens

<400> SEQUENCE: 5
tcttcgccga gagtcgtcgg ggtttcctgc ttcaacagtg cttggacgga acccggc        57

<210> SEQ ID NO 6
<211> LENGTH: 42
<212> TYPE: DNA
<213> ORGANISM: Artificial sequence
<220> FEATURE:
<223> OTHER INFORMATION: consensus sequence
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (8)..(14)
<223> OTHER INFORMATION: n is a, c, g, or t
<220> FEATURE:
<221> NAME/KEY: misc_feature
```

```
<222> LOCATION: (16)..(20)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (38)..(41)
<223> OTHER INFORMATION: n is a, c, g, or t

<400> SEQUENCE: 6
gnnnnngnnn nnnncnnnnn canngnnngg ncgnnncnnn nc                42

<210> SEQ ID NO 7
<211> LENGTH: 46
<212> TYPE: DNA
<213> ORGANISM: Homo sapiens

<400> SEQUENCE: 7
cggggtttcc tgcttcaaca gtgcttggac ggaacccggc gctcgt            46

<210> SEQ ID NO 8
<211> LENGTH: 46
<212> TYPE: DNA
<213> ORGANISM: Homo sapiens

<400> SEQUENCE: 8
gtctgtctct tgcttcaaca gtgtttggac ggaacagatc cgggga            46

<210> SEQ ID NO 9
<211> LENGTH: 46
<212> TYPE: DNA
<213> ORGANISM: Homo sapiens

<400> SEQUENCE: 9
ggagtggcca ttcgacgaca gtgtggtgta aaggaattca ttagcc            46

<210> SEQ ID NO 10
<211> LENGTH: 46
<212> TYPE: DNA
<213> ORGANISM: Homo sapiens

<400> SEQUENCE: 10
cggcggtggc ggcgcgggca gagcaaggac gcggcggatc ccactc            46

<210> SEQ ID NO 11
<211> LENGTH: 13
<212> TYPE: DNA
<213> ORGANISM: Artificial Sequence
<220> FEATURE:
<223> OTHER INFORMATION: loop sequence

<400> SEQUENCE: 11
cagagcaagg acg                                                13
```

```
<210> SEQ ID NO 12
<211> LENGTH: 53
<212> TYPE: RNA
<213> ORGANISM: Homo sapiens

<400> SEQUENCE: 12
acugggagug gccauucgac gacagugugg uguaaaggaa uucauuagcc aug          53

<210> SEQ ID NO 13
<211> LENGTH: 55
<212> TYPE: RNA
<213> ORGANISM: Mus musculus

<400> SEQUENCE: 13
uccacgcagc cagaagucgg aaagugugga gcaaaaauac aucuuauuag ccaug        55

<210> SEQ ID NO 14
<211> LENGTH: 55
<212> TYPE: RNA
<213> ORGANISM: Rattus norvegicus

<400> SEQUENCE: 14
gaguucugcg gaagccuaga gagccgugug gagcaaagau acaucuuuag ccaug        55

<210> SEQ ID NO 15
<211> LENGTH: 53
<212> TYPE: RNA
<213> ORGANISM: Bos taurus

<400> SEQUENCE: 15
accgagcgcg gcgacgccgg gugagugugg uguaaaggaa uucguuagcc aug          53

<210> SEQ ID NO 16
<211> LENGTH: 53
<212> TYPE: RNA
<213> ORGANISM: Canis Lupus

<400> SEQUENCE: 16
ccgagcgcgg cagcgugggg gugagugugg ugugaacgaa uucauuagcc aug          53

<210> SEQ ID NO 17
<211> LENGTH: 53
<212> TYPE: RNA
<213> ORGANISM: Gallus gallus

<400> SEQUENCE: 17
ccuuccugca gcggcggacc cggcguuuug ugugaagaaa uccuucagcc aug          53

<210> SEQ ID NO 18
<211> LENGTH: 53
<212> TYPE: RNA
<213> ORGANISM: Homo sapiens

<400> SEQUENCE: 18
ucgucggggu uccugcuuc aacagugcuu ggacggaacc cggcgcucgu uuc           53

<210> SEQ ID NO 19
<211> LENGTH: 53
<212> TYPE: RNA
<213> ORGANISM: Homo sapiens

<400> SEQUENCE: 19 gcggguccugu cucuugcuuc aacaguguuu ggacggaaca gauccgggga cuc         53
```

<210> SEQ ID NO 20
<211> LENGTH: 55
<212> TYPE: RNA
<213> ORGANISM: Homo sapiens

<400> SEQUENCE: 20
cggcggcggu ggcggcgcgg gcagagcaag gacgcggcgg aucccacucg cacuc    55

<210> SEQ ID NO 21
<211> LENGTH: 86
<212> TYPE: RNA
<213> ORGANISM: Homo sapiens

<400> SEQUENCE: 21
gucgccuguc cuccgagcca gucgcugaca gccgcggcgc cgcgagcuuc uccucuccuc    60
acgaccgagg cagagcaguc auuaug    86

<210> SEQ ID NO 22
<211> LENGTH: 82
<212> TYPE: RNA
<213> ORGANISM: Gorilla gorilla

<400> SEQUENCE: 22
gucgccuguc cuccgagcca gucgcugaca gccgcggcgc cgcgagcuuc uccucuccuc    60
acgaccgaga gcagucauca ug    82

<210> SEQ ID NO 23
<211> LENGTH: 82
<212> TYPE: RNA
<213> ORGANISM: Pan paniscus

<400> SEQUENCE: 23
gucgccgguc cuccgagcca gucgcugaca gccgcggcgc cgcgagcuuc uccucuccuc    60
acgaccgaga gcagucauca ug    82

<210> SEQ ID NO 24
<211> LENGTH: 86
<212> TYPE: RNA
<213> ORGANISM: Macaca fascicularis

<400> SEQUENCE: 24
gucgccugcc cuccgcgcca guagcugaca gccgcggcgc cgcgagcuuc uccucuccuc    60
acgaccgagg cagaacaguc aucaug    86

<210> SEQ ID NO 25
<211> LENGTH: 46
<212> TYPE: RNA
<213> ORGANISM: Homo sapiens

<400> SEQUENCE: 25
gucugucucu ugcuucaaca guguuuggac ggaacagauc cgggga    46

<210> SEQ ID NO 26
<211> LENGTH: 46
<212> TYPE: RNA
<213> ORGANISM: Homo sapiens

<400> SEQUENCE: 26
cgggguuucc ugcuucaaca gugcuuggac ggaacccggc gcucgu    46

```
<210> SEQ ID NO 27
<211> LENGTH: 31
<212> TYPE: RNA
<213> ORGANISM: Homo sapiens

<400> SEQUENCE: 27
ggcggcgcgg gcagagcaag gacgcggcgg a                                31

<210> SEQ ID NO 28
<211> LENGTH: 66
<212> TYPE: RNA
<213> ORGANISM: Bos taurus

<400> SEQUENCE: 28
gccagucgcu gacagccgca gagcugagag cgucuucucu cucgcagaag cagauaaguc   60
aucaug                                                             66

<210> SEQ ID NO 29
<211> LENGTH: 65
<212> TYPE: RNA
<213> ORGANISM: ovis aries

<400> SEQUENCE: 29
ugccagucgc ugacagccgc agagcugaga gcgucuucuc ucccagaggc agagaaguca   60
ucaug                                                              65

<210> SEQ ID NO 30
<211> LENGTH: 59
<212> TYPE: RNA
<213> ORGANISM: Rattus norvegicus

<400> SEQUENCE: 30
gcguugucag agcagcagac ggagucgagc gucgcgucgg uggcagauca gccaucaug    59

<210> SEQ ID NO 31
<211> LENGTH: 62
<212> TYPE: RNA
<213> ORGANISM: Mus musculus

<400> SEQUENCE: 31
uugucggauc agcagaccga uucugggcgc ugcgucgcau cgguggcaga ucagucauca   60
ug                                                                 62

<210> SEQ ID NO 32
<211> LENGTH: 84
<212> TYPE: RNA
<213> ORGANISM: Homo sapiens

<400> SEQUENCE: 32
gccgagaccg cguccgcccc gcgagcacag agccucgccu uugccgaucc gccgccguc    60 cacaccegcc gccagcucac caug                                         84
```

What is claimed is:

1. A method of ameliorating Prion's disease in a human patient, comprising administering a pharmaceutical composition consisting of posiphen or a pharmaceutically acceptable salt thereof in an amount from about 0.1 mg/day to about 30 mg/day together with one or more pharmaceutically acceptable excipients, on a once a day basis to a human patient suffering from Prion's disease.

2. The method of claim 1, wherein posiphen or a pharmaceutically acceptable salt thereof is administered orally in an amount from about 1 mg to about 30 mg on a once a day basis.

3. The method of claim 1, wherein posiphen or a pharmaceutically acceptable salt thereof is administered parenterally in an amount from about 0.5 mg to about 30 mg/day.

4. The method of claim 1, wherein posiphen or a pharmaceutically acceptable salt thereof is administered intravenously in an amount from about 0.1 mg/day to about 25 mg/day.

5. The method of claim 1, wherein posiphen or a pharmaceutically acceptable salt thereof is administered intramuscularly in an amount from about 0.3 mg/day to about 30 mg/day.

6. The method of claim 1, wherein the peak plasma circulating level ranges of posiphen are from about 10 ng/mL to about 160 ng/ml in the human patient.

7. The method of claim 1, wherein the peak plasma circulating level of posiphen is reached within about 6 hours after said administering the pharmaceutical composition.

8. The method of claim 1, wherein the plasma circulating level of posiphen is equal to or greater than about 20 ng/mL for at least 9 hours after administering the pharmaceutical composition.

9. The method of claim 1, wherein the administration results in a brain level of posiphen that ranges from about 4 to about 10 times the plasma level of posiphen in the human patient.

10. The method of claim 1, wherein the half-life of posiphen in cerebrospinal fluid after administering is about 12 hours.

11. The method of claim 1, wherein the half-life of posiphen in plasma after administering is about 5 hours.

12. The method of claim 1, wherein the pharmaceutical composition is selected from the group consisting of tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, and a composition for intravesical administration.

13. The method of claim 1, wherein the pharmaceutical composition inhibits the production of prions in the human.

14. The method of claim 2, wherein the pharmaceutical composition inhibits the production of prions in the human.

15. The method of claim 1, wherein the Prion's disease is selected from the group consisting of scrapie prion; transmissible mink encephalopathy (TME) prion; chronic wasting disease (CWD) prion; bovine spongiform encephalopathy (BSE) prion; feline spongiform encephalopathy (FSE) prion; exotic ungulate encephalopathy (EUE) prion; kuru prion; Creutzfeldt-Jakob disease (CJD) or Variant Creutzfeldt-Jakob disease (vCJD, nvCJD) prion; Gerstmann-Straussler-Scheinker syndrome (GSS) prion; and fatal familial insomnia (FFI) prion.

* * * * *